(12) United States Patent
Fishkin

(10) Patent No.: US 9,624,240 B2
(45) Date of Patent: Apr. 18, 2017

(54) MAYTANSINOID DERIVATIVES WITH SULFOXIDE LINKER

(71) Applicant: ImmunoGen, Inc., Waltham, MA (US)

(72) Inventor: Nathan Fishkin, Weymouth, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 14/718,350

(22) Filed: May 21, 2015

(65) Prior Publication Data

US 2016/0031902 A1 Feb. 4, 2016

Related U.S. Application Data

(62) Division of application No. 14/009,957, filed as application No. PCT/US2012/029791 on Mar. 20, 2012, now Pat. No. 9,156,854.

(60) Provisional application No. 61/504,953, filed on Jul. 6, 2011, provisional application No. 61/476,529, filed on Apr. 18, 2011.

(51) Int. Cl.
| | |
|---|---|
| *A61K 38/00* | (2006.01) |
| *C07D 498/04* | (2006.01) |
| *C07D 498/18* | (2006.01) |
| *A61K 31/537* | (2006.01) |
| *A61K 45/06* | (2006.01) |
| *A61K 47/48* | (2006.01) |
| *A61K 31/5365* | (2006.01) |

(52) U.S. Cl.
CPC .......... *C07D 498/04* (2013.01); *A61K 31/537* (2013.01); *A61K 31/5365* (2013.01); *A61K 45/06* (2013.01); *A61K 47/48384* (2013.01); *A61K 47/48561* (2013.01); *C07D 498/18* (2013.01)

(58) Field of Classification Search
CPC ........ A61K 47/48384; A61K 39/39558; A61K 47/48438; A61K 39/3955; A61K 38/00
See application file for complete search history.

(56) References Cited

U.S. PATENT DOCUMENTS

| | | |
|---|---|---|
| 5,985,837 A | 11/1999 | Ritter et al. |
| 2002/0183334 A1 | 12/2002 | Bacon et al. |
| 2005/0276812 A1 | 12/2005 | Ebens, Jr. et al. |
| 2009/0036431 A1 | 2/2009 | Gauzy et al. |
| 2010/0316656 A1 | 12/2010 | Bouchard et al. |

OTHER PUBLICATIONS

International Search Report for PCT/US2012/029791 dated Jun. 19, 2012.

*Primary Examiner* — James H Astrum Acevedo
*Assistant Examiner* — Kaipeen Yang
(74) *Attorney, Agent, or Firm* — Sughrue Mion, PLLC

(57) ABSTRACT

The invention relates to novel maytansinoid compounds having sulfoxide linkers and more specifically to novel maytansinoid compounds of structural formula (I) and (II). The invention also provides conjugates of the maytansinoid compounds linked to a cell-binding agent. The invention further provides compositions and methods useful for inhibiting abnormal cell growth or treating a proliferative disorder in a mammal using the compounds or conjugates of the invention.

18 Claims, 8 Drawing Sheets

IgG1-SMCC-DM1 (1) and IgG-sulfoxide-DM1 (2a) cell killing activity against A431 squamous cell carcinoma in vitro. Conjugate 2a (thioether partially oxidized selectively to the sulfoxide) is ~ 2-fold more potent than the parent conjugate 1a.

FIG. 2 anti-EpCAM-SMCC-DM1 (1) and anti-EpCAM-sulfoxide-DM1 (2b) cell killing activity against PC9 lung carcinoma cells in vitro. Conjugate 2b (thioether partially oxidized selectively to the sulfoxide) is ~ 3-fold more potent than the parent conjugate 1b. Preincubation of PC9 cells with 1 μM unconjugated anti-EpCAM antibody (to fully block antigen binding sites) leads to significantly reduced cell killing activity for conjugates 1b and 2b. Therefore, the additional activity of 2b over 1b is antigen dependant.

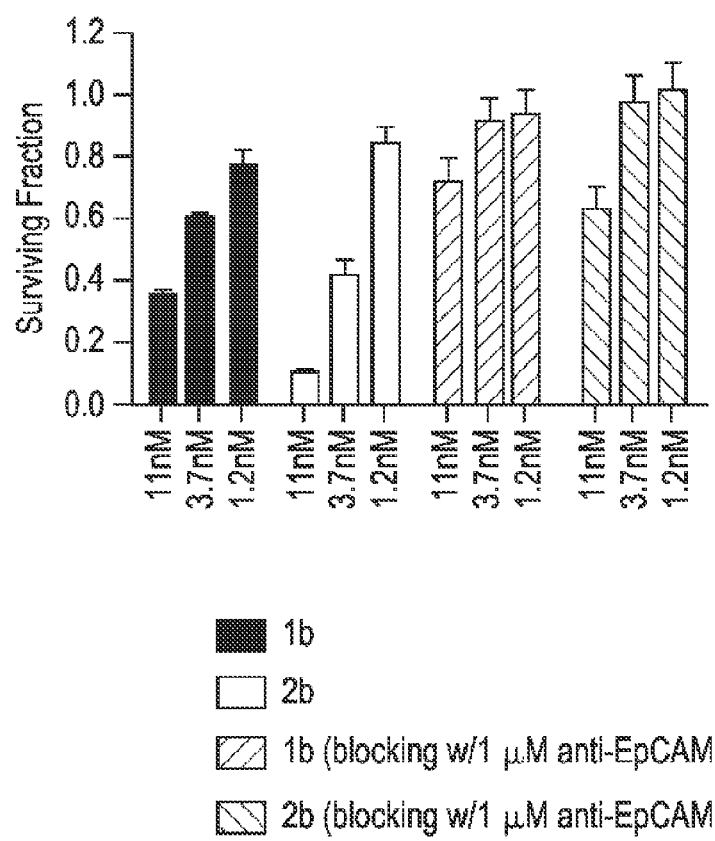

Hypothetical scheme explaining observed additional antigen-specific activity of sulfoxide linked AMCs over thioether linker AMCs.

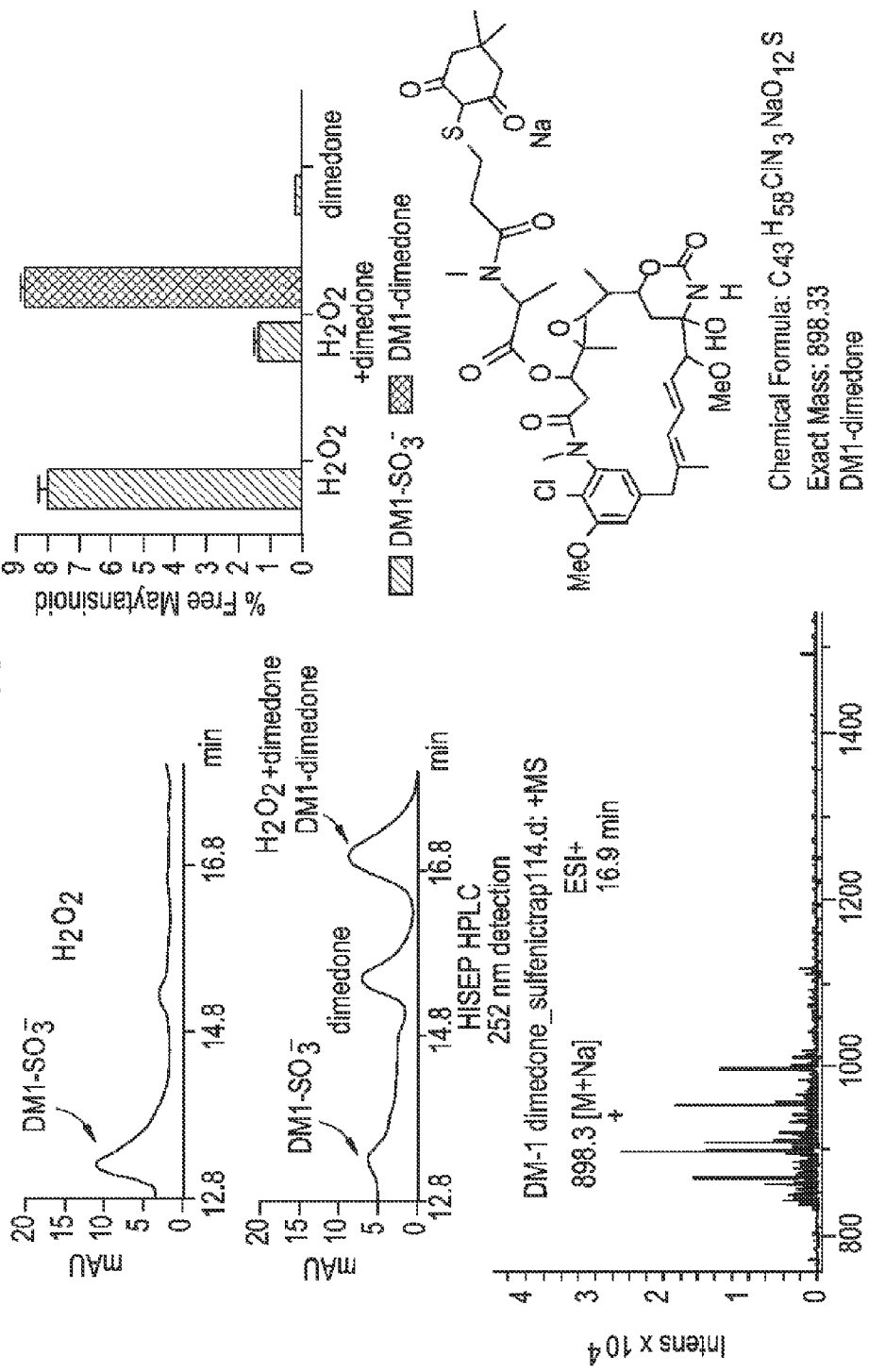
FIG. 4 HPLC and MS data showing formation of DM1-dimedone upon free maytansinoid release from oxidized Ab-SMCC-DM1 conjugate 2 after 12 h at 37°C.

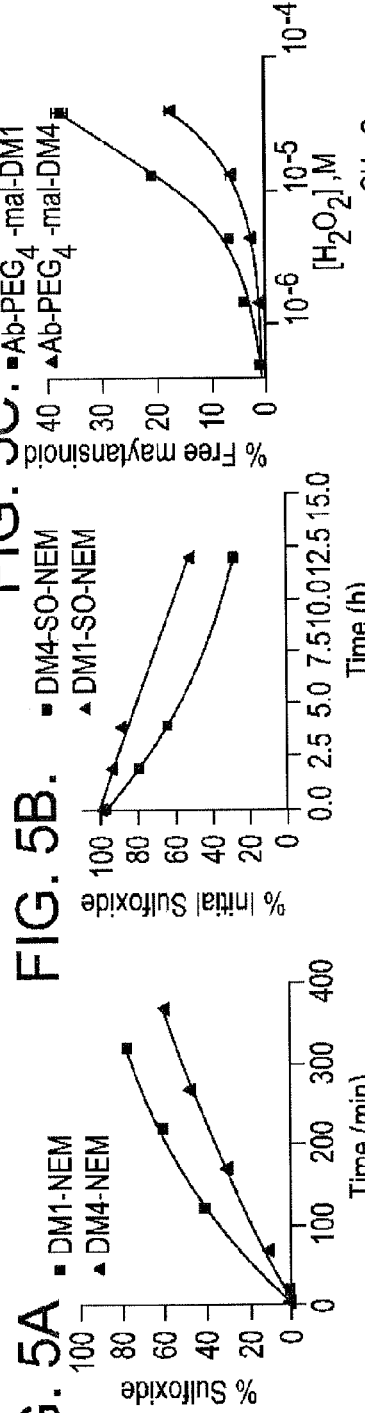

Rate comparison of model thioether oxidation (A), model sulfoxide elimination (B) and free maytansinoid formation from Ab-PEG4-mal-DMx conjugate (C) for unhindered (DM1) and hindered (DM4) maytansinoid thioethers. Thioether formed with hindered thiol DM4 oxidizes 2-fold slower and undergoes sulfoxide elimination 2-fold slower than corresponding thioether formed from unhindered DM1 thiol. The observation that Ab-PEG4-mal-DM4 is ~5-fold more resistant to oxidation promoted free maytansinoid release than Ab-PEG4-mal-DM1 (panel C) is consistent with the observed rates of sulfoxide formation and beta-elimination. Panel D shows reaction scheme for Ab-PEG4-mal-DMx oxidation promoted maytansinoid release.

LC-MS analysis of thermal and reductive stability of DM1-NEM and DM1-SO-NEM.

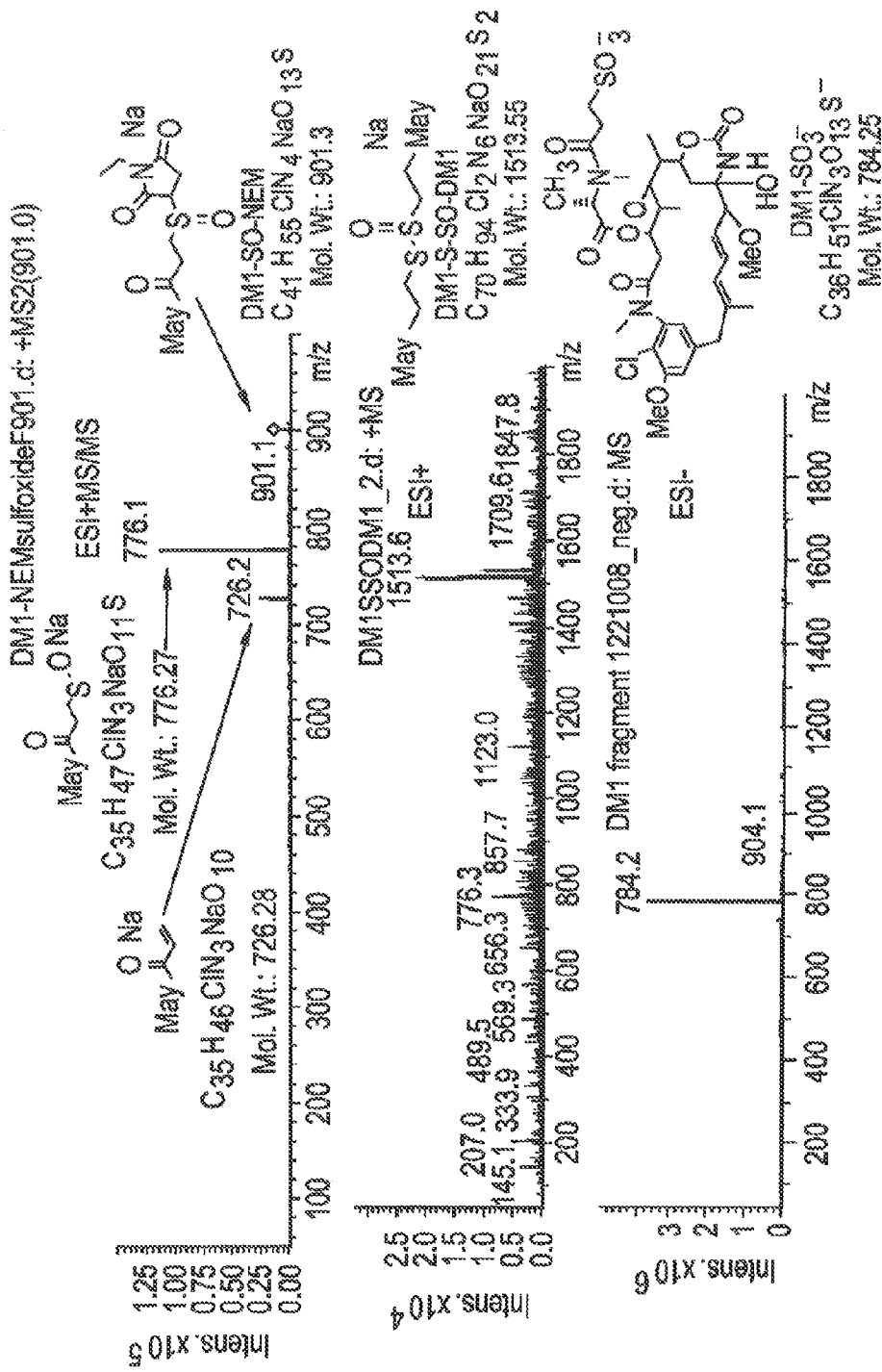
FIG. 6B ESI-MS spectra for DM1-SO-NEM, DM1-S-SO-DM1 and DM1-SO3−

Rate data for sulfoxide elimination from DM1-SO-NEM.

SEQUENCE LISTING

```
<160> NUMBER OF SEQ ID NOS: 11

<210> SEQ ID NO 1
<211> LENGTH: 448
<212> TYPE: PRT
<213> ORGANISM: Artificial Sequence
<220> FEATURE:
<223> OTHER INFORMATION: heavy chain of human folate receptor 1

<400> SEQUENCE: 1

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 2
<211> LENGTH: 118
<212> TYPE: PRT
<213> ORGANISM: Artificial Sequence
<220> FEATURE:
<223> OTHER INFORMATION: heavy chain variable domain

<400> SEQUENCE: 2

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110
```

```
Thr Val Thr Val Ser Ser
        115

<210> SEQ ID NO 3
<211> LENGTH: 112
<212> TYPE: PRT
<213> ORGANISM: Artificial Sequence
<220> FEATURE:
<223> OTHER INFORMATION: light chain variable domain

<400> SEQUENCE: 3

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 4
<211> LENGTH: 112
<212> TYPE: PRT
<213> ORGANISM: Artificial Sequence
<220> FEATURE:
<223> OTHER INFORMATION: light chain variable domain

<400> SEQUENCE: 4

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 5
<211> LENGTH: 5
<212> TYPE: PRT
<213> ORGANISM: Artificial Sequence
<220> FEATURE:
<223> OTHER INFORMATION: heavy chain CDR1

<400> SEQUENCE: 5

Gly Tyr Phe Met Asn
1               5
```

```
<210> SEQ ID NO 6
<211> LENGTH: 17
<212> TYPE: PRT
<213> ORGANISM: Artificial Sequence
<220> FEATURE:
<223> OTHER INFORMATION: heavy chain CDR2
<220> FEATURE:
<221> NAME/KEY: MISC_FEATURE
<222> LOCATION: (14)..(14)
<223> OTHER INFORMATION: K, Q, or H
<220> FEATURE:
<221> NAME/KEY: MISC_FEATURE
<222> LOCATION: (16)..(16)
<223> OTHER INFORMATION: Q, H, N, or R
<220> FEATURE:
<221> NAME/KEY: MISC_FEATURE
<222> LOCATION: (17)..(17)
<223> OTHER INFORMATION: G, E, T, S, A, or V

<400> SEQUENCE: 6

Arg Ile His Pro Tyr Asp Gly Asp Thr Phe Tyr Asn Gln Xaa Phe Xaa
1               5                   10                  15

Xaa

<210> SEQ ID NO 7
<211> LENGTH: 9
<212> TYPE: PRT
<213> ORGANISM: Artificial Sequence
<220> FEATURE:
<223> OTHER INFORMATION: heavy chain CDR3

<400> SEQUENCE: 7

Tyr Asp Gly Ser Arg Ala Met Asp Tyr
1               5

<210> SEQ ID NO 8
<211> LENGTH: 15
<212> TYPE: PRT
<213> ORGANISM: Artificial Sequence
<220> FEATURE:
<223> OTHER INFORMATION: light chain CDR1

<400> SEQUENCE: 8

Lys Ala Ser Gln Ser Val Ser Phe Ala Gly Thr Ser Leu Met His
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: light chain CDR2

<400> SEQUENCE: 9

Arg Ala Ser Asn Leu Glu Ala
1               5

<210> SEQ ID NO 10
<211> LENGTH: 9
<212> TYPE: PRT
<213> ORGANISM: Artificial Sequence
<220> FEATURE:
<223> OTHER INFORMATION: light chain CDR3

<400> SEQUENCE: 10

Gln Gln Ser Arg Glu Tyr Pro Tyr Thr
1               5
```

```
<210> SEQ ID NO 11
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 11

Arg Ile His Pro Tyr Asp Gly Asp Thr Phe Tyr Asn Gln Lys Phe Gln
1               5                   10                  15

Gly
```

MAYTANSINOID DERIVATIVES WITH SULFOXIDE LINKER

CROSS REFERENCE TO RELATED APPLICATIONS

This application is a Divisional of U.S. application Ser. No. 14/009,957, filed Oct. 4, 2013 (now allowed); which is a National Stage of International Application No. PCT/US2012/029791 filed Mar. 20, 2012, claiming priority based on U.S. Provisional Application No. 61/504,953 filed Jul. 6, 2011, and U.S. Provisional Application No. 61/476,529 filed Apr. 18, 2011; the contents of all of which are incorporated herein by reference in their entirety

FIELD OF THE INVENTION

The present invention relates to novel cytotoxic compounds and cytotoxic conjugates comprising these cytotoxic compounds and cell-binding agents. More specifically, this invention relates to novel maytansinoid compounds, derivatives thereof, intermediates thereof, conjugates thereof, and pharmaceutically acceptable salts thereof, which are useful as medicaments, in particular as anti-proliferative agents.

BACKGROUND OF THE INVENTION

Antibody-drug conjugates (ADC) are emerging as a powerful class of anti-tumor agents with efficacy across a range of cancers. ADCs are commonly composed of three distinct elements: a cell-binding agent; a linker; and a cytotoxic agent. The linker component of ADC is an important element in developing targeted anti-cancer agents that possess an optimal therapeutic window: high activity at a low, non-toxic dose.

Therefore, there is a need for ADCs having new class of linker component.

SUMMARY OF THE INVENTION

One embodiment of the present invention is directed to a compound represented by structural formula (I'):

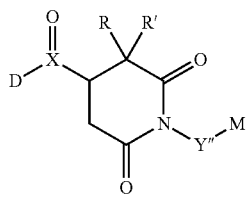

wherein:
D is a cytotoxic agent;
X is S or Se;
R and R' are each independently selected from the group consisting of —H, an alkyl, a cycloalkyl, —OR$^a$, and —NR$^b$R$^c$;
R$^a$, R$^b$ and R$^c$ are each independently H or an alkyl;
p is 0, 1 or 2
Y" is a spacer;
M is a linking group that can react with a cell-binding agent to form a covalent bond.

One embodiment of the present invention is directed to a compound represented by structural formula (I):

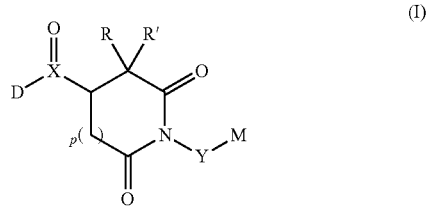

wherein:
D is a cytotoxic agent;
X is S or Se;
R and R' are each independently selected from the group consisting of —H, an alkyl, a cycloalkyl, —OR$^a$, and —NR$^b$R$^c$;
R$^a$, R$^b$ and R$^c$ are each independently H or an alkyl;
p is 0, 1 or 2
Y is an alkylene, a polyethylene glycol unit represented by —(CH$_2$—CH$_2$—O)$_n$—R$^d$—, —R$^d$-E- or —R$^d$—W—R$^e$—,
n is an integer from 1 to 24;
E is a cycloalkyl, a heterocyclyl, an aryl or a heteroaryl,
W is —C(=O)NH—, —NHC(=O)—, —(C=O)O— or —O(C=O)—,
R$^d$ is absent or an alkyl;
R$^e$ is an alkyl;
M is a linking group that can react with a cell-binding agent to form a covalent bond.

In another embodiment, the present invention is directed to a compound of structural formula (II):

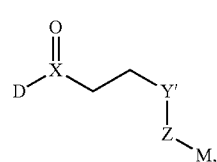

wherein:
D is a cytotoxic agent;
X is S or Se;
Y' is —SO$_2$—, aryl, pyridyl or —C(=O)—;
Z is an alkyl, a cycloalkyl, a heterocyclyl, an aryl, a heteroaryl, or —N(R$^{b_1}$)—R$^{d_1}$—;
R$^{b_1}$ is H or a C$_{1-4}$ alkyl;
R$^{d_1}$ is a C$_{1-4}$ alkyl; and
M is a linking group that can react with a cell-binding agent to form a covalent bond.

The present invention is also directed to conjugates comprising a cell-binding agent chemically linked to a compound of structural formula (I'), (I) or (II). In one embodiment, the conjugate is represented by the following structural formula:

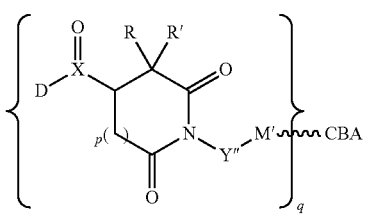

(III')

wherein:

CBA represents a cell-binding agent;

D is a cytotoxic agent;

X is S or Se;

R and R' are each independently selected from the group consisting of —H, an alkyl, a cycloalkyl, —OR$^a$, and —NR$^b$R$^c$;

R$^a$, R$^b$ and R$^c$ are each independently H or an alkyl;

p is 0, 1 or 2;

Y" is a spacer;

q is an integer from 1 to 20; and

M' is a linking moiety.

In another embodiment, the conjugate is represented by the following structural formula:

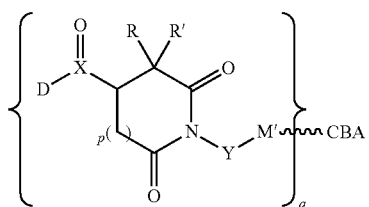

(III)

wherein:

CBA represents a cell-binding agent;

D is a cytotoxic agent;

X is S or Se;

R and R' are each independently selected from the group consisting of —H, an alkyl, a cycloalkyl, —OR$^a$, and —NR$^b$R$^c$;

R$^a$, R$^b$ and R$^c$ are each independently H or an alkyl;

p is 0, 1 or 2

Y is an alkylene, a polyethylene glycol unit represented by —(CH$_2$—CH$_2$—O)$_n$—R$^d$—, —R$^d$-E- or —R$^d$—W—R$^e$—, n is an integer from 1 to 24;

E is a cycloalkyl, a heterocyclyl, an aryl or a heteroaryl,

W is —C(=O)NH—, —NHC(=O)—, —(C=O)O— or —O(C=O)—,

R$^d$ is absent or an alkyl;

R$^e$ is an alkyl;

q is an integer from 1 to 20; and

M' is a linking moiety.

In another embodiment, the conjugate is represented by the following structural formula:

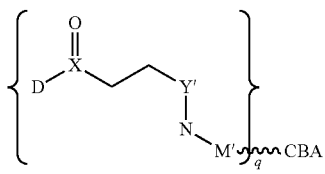

(IV)

wherein:

D is a cytotoxic agent;

X is S or Se;

Y' is —SO$_2$—, aryl, pyridyl or —C(=O)—;

Z is an alkyl, a cycloalkyl, a heterocyclyl, an aryl, a heteroaryl, or —N(R$^{b_1}$)—R$^{d_1}$—;

R$^{b_1}$ is H or a C$_{1-4}$ alkyl;

R$^{d_1}$ is a C$_{1-4}$ alkyl;

q is an integer from 1 to 20; and

M' is a linking moiety.

The present invention is also directed to a pharmaceutical composition comprising the conjugates described herein and a pharmaceutically acceptable carrier.

In another embodiment, the present invention is directed to a method of inhibiting abnormal cell growth or treating a proliferative disorder, an autoimmune disorder, a destructive bone disorder, an infectious disease, a viral disease, a fibrotic disease, a neurodegenerative disorder, a pancreatitis or kidney disease in a mammal comprising administering to the mammal a therapeutically effective amount of the conjugate described herein and optionally in combination with another chemotherapeutic agent.

In another embodiment, the present invention is directed to a cytotoxic compound or a conjugate described herein for use in inhibiting abnormal cell growth or in treating a proliferative disorder, an autoimmune disorder, a destructive bone disorder, an infectious disease, a viral disease, a fibrotic disease, a neurodegenerative disorder, a pancreatitis or kidney disease in a mammal.

BRIEF DESCRIPTION OF THE FIGURES

FIG. 2 shows in vitro cytotoxicity of anti-EpCAM-SMCC-sulfoxide-DM1 conjugate (2b) having a sulfoxide linker as compared to anti-EpCAM-SMCC-DM1 conjugate (1b) having a thioether linker in lung carcinoma cell line PC9.

FIG. 4 shows HPLC and MS data indicating the formation of DM1-dimedone (DM1-NME) upon free maytansinoid release from the oxidized Ab-SMCC-DM1 conjugate 2 after 12 h at 37° C.

FIGS. 5A-5D show rate comparison of model thioether oxidation (A), model sulfoxide elimination (B) and free maytansinoid formation for Ab-PEG$_4$-mal-DM$_x$ conjugate (C) for unhindered DM1 and hindered DM4 maytansinoid thioethers. (D) shows a reaction scheme for oxidation promoted maytansinoid release from Ab-PEG$_4$-mal-DM$_x$.

FIGS. 6A-6C show HPLC traces (A), ESI-MS data (B), and rate of conversion (C) of DM1 SO-NEM to DM1-SO3- and DM1-S-SO-DM1 under elevated temperature (37 C) and/or reducing conditions (dithiothreitol) in PBS pH 7.4. Control compound DM1-NEM was stable under these tested reaction conditions.

DETAILED DESCRIPTION OF THE INVENTION

Figure 1:
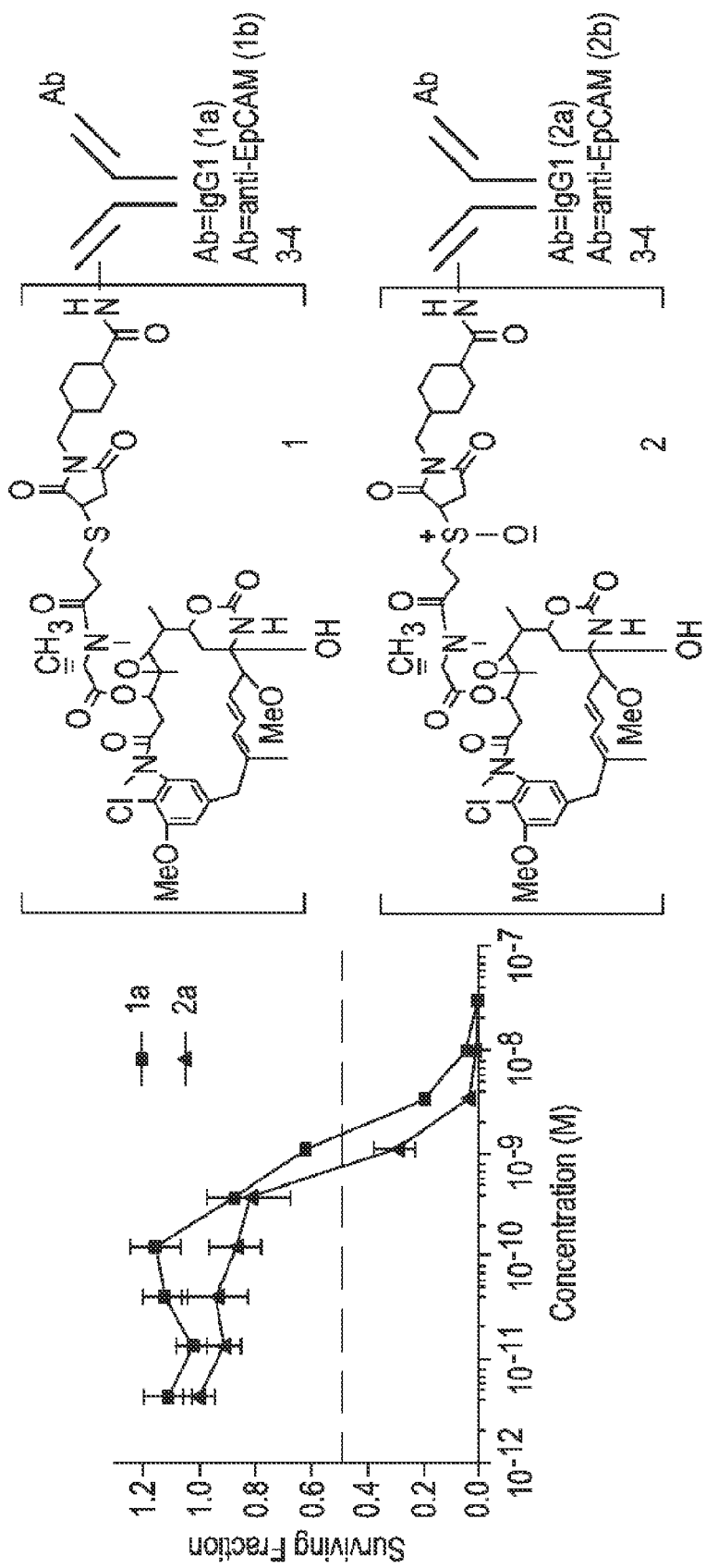
FIG. 1 shows in vitro cytotoxicity of IgG1-SMCC-sulfoxide-DM1 conjugate (2a) having a sulfoxide linker as compared to IgG1-SMCC-DM1 conjugate (1a) having a thioether linker in squamous cell carcinoma cell line A431.
Figure 3:
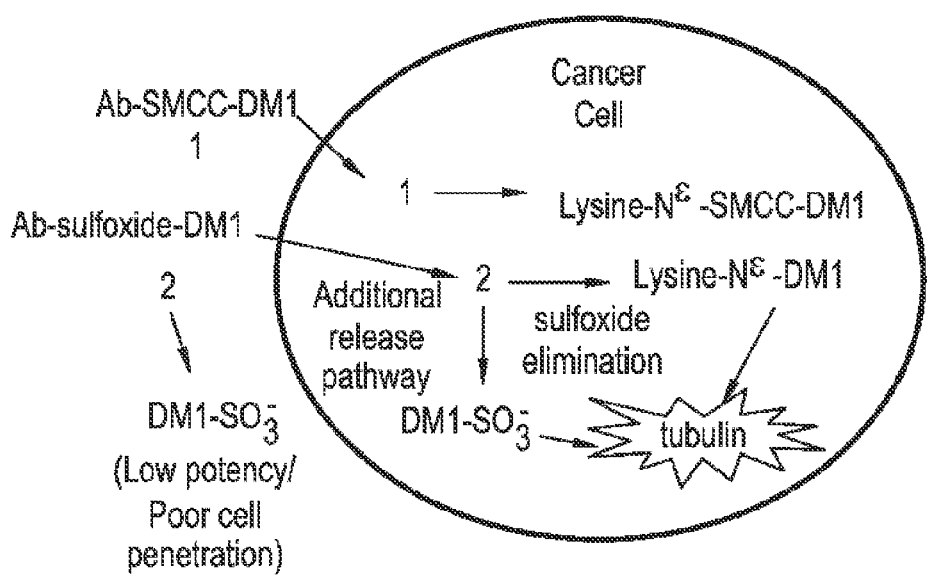
FIG. 3 depicts a hypothetical scheme for explaining the observed higher antigen-specific activity of conjugate (2) as compared to conjugate (1).
Figure 6A:
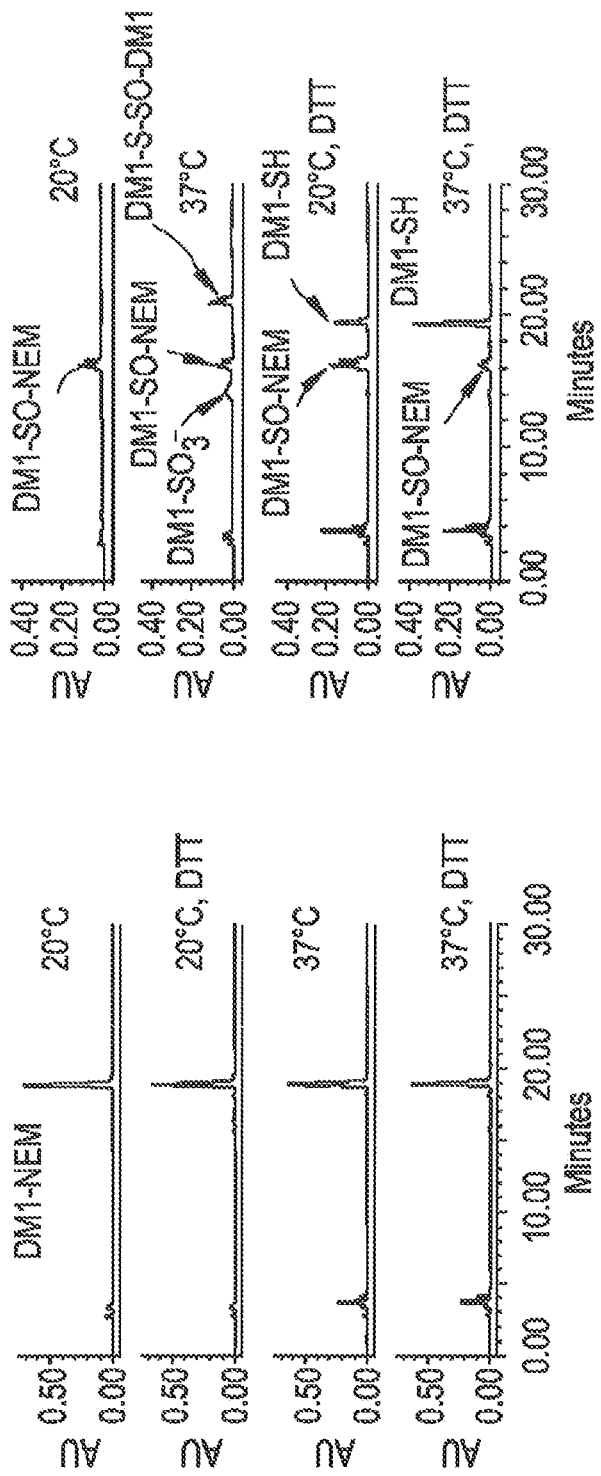
Figure 6C:
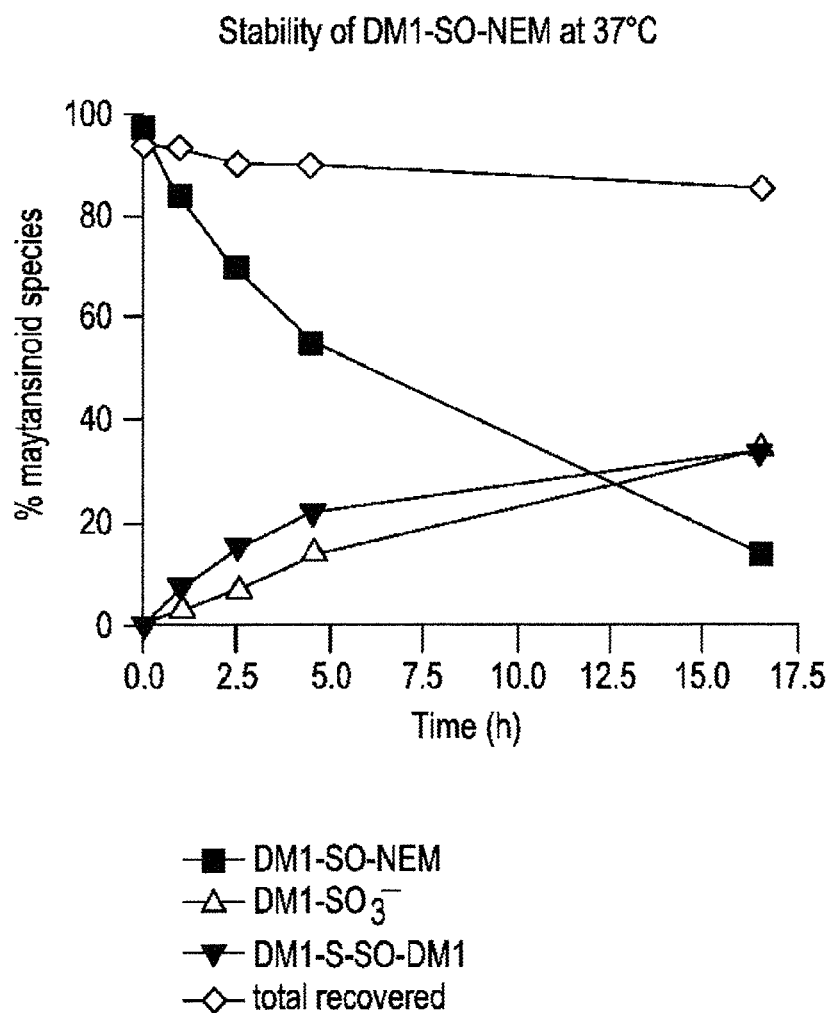

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

DEFINITIONS

"Alkyl" as used herein refers to a saturated aliphatic linear or branched-chain monovalent hydrocarbon radical having one to twenty carbon atoms. Examples of alkyl include, but are not limited to, methyl, ethyl, 1-propyl, 2-propyl, 1-butyl, 2-methyl-1-propyl, —CH$_2$CH(CH$_3$)$_2$, 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms, also referred to as "C$_{1-10}$ alkyl". More preferably, the alkyl has one to six carbon atoms, also referred to as "C$_{1-6}$ alkyl". Even more preferably, the alkyl has one to four carbon atoms, also referred to as "C$_{1-4}$ alkyl".

"Alkenyl" as used herein refers to aliphatic linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like. Preferably, the alkenyl has two to ten carbon atoms, also referred to as "C$_{2-10}$ alkenyl". More preferably, the alkyl has two to four carbon atoms, also referred to as "C$_{2-4}$ alkenyl".

"Alkynyl" as used herein refers to aliphatic linear or branched-chain monovalent hydrocarbon radical of two to twenty carbon atoms with at least one carbon-carbon triple bond. Examples include, but are not limited to ethynyl, propynyl, 1-butynyl, 2-butynyl, 1-pentynyl, 2-pentynyl, 3-pentynyl, hexynyl, and the like. Preferably, the alkynyl has two to ten carbon atoms, also referred to as "C$_{2-10}$ alkynyl". More preferably, the alkynyl has two to four carbon atoms, also referred to as "C$_{2-4}$ alkynyl".

The term "alkylene" refers to a saturated aliphatic linear or branched-chain divalent hydrocarbon radical having one to twenty carbon atoms. Preferably, the alkylene has one to ten carbon atoms. More preferably, the alkylene has one to four carbon atoms.

The term "carbocycle", "carbocyclyl" and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-I-enyl, 1-cyclopent-2-enyl, 1-cyclopent-3-enyl, cyclohexyl, 1-cyclohex-I-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "cyclic alkyl" and "cycloalkyl" can be used interchangeably. They refer to a monovalent saturated carbocyclic ring radical. Preferably, the cycloalkyl is 3 to 7 membered monocyclic ring radical. More preferably, the cycloalkyl is cyclohexyl.

"Aryl" as used herein means a monovalent monocyclic or polycyclic (e.g. bicyclic or tricyclic) aromatic hydrocarbon radical of 6-18 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclcyl can include the oxidized forms such as NO, SO, and $SO_2$.

The term "halo" or "halogen" refers to F, Cl, Br or I.

The alkyl, alkenyl, cycloalkyl, carbocyclyl, aryl, heterocyclyl and heteroaryl described above can be optionally substituted with one more (e.g., 2, 3, 4, 5, 6 or more) suitable substituents. In one embodiment, the alkyl, alkenyl, cycloalkyl, carbocyclyl, aryl, heterocyclyl and heteroaryl described above is unsubstituted. In another embodiment, the alkyl, alkenyl, cycloalkyl, carbocyclyl, aryl, heterocyclyl and heteroaryl described above are substituted with one more (e.g., 2, 3, 4, 5, 6 or more) suitable substituents.

Such suitable substituents, in non-limiting examples, can be selected from an alkyl, alkenyl or alkynyl having from 1 to 10 carbon atoms, cycloalkyl, aryl, heteroaryl, heterocyclyl, halogen, guanidinium [—NH(C=NH)NH$_2$], —OR$^{100}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)$_n$R$^{101}$ wherein M is H or a cation (such as Na$^+$ or K$^+$); R$^{100}$, R$^{101}$, R$^{102}$ and R$^{103}$ are each independently selected from H, alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocycyclyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, CN, NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, CN, NR$^{102}$R$^{103}$, CF$_3$, OR$^{101}$, aryl, heteroaryl, heterocycycl, SR$^{101}$, SOR$^{101}$, SO$_2$R$^{101}$ and —SO$_3$M. Preferably, the suitable substituent is selected from the group consisting of -halogen, —OH, —NO$_2$, —CN, C$_{1-4}$ alkyl, —OR$^{100}$, NR$^{101}$R$^{102}$, —NR$^{101}$COR$^{102}$, —SR$^{100}$, —SO$_2$R$^{101}$, —SO$_2$NR$^{101}$R$^{102}$, —COR$^{101}$, —OCOR$^{101}$ and —OCONR$^{101}$R$^{102}$ wherein R$^{100}$, R$^{101}$ and R$^{102}$ are each independently —H or C$_{1-4}$ alkyl.

The term "compound" and "cytotoxic compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers", "geometric isomers", "tautomers", "solvates", "metabolites", "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "linkable to a cell binding agent" as used herein refers to the compounds described herein or derivates thereof comprising at least one linking group or a precursor thereof suitable to bond these compounds or derivatives thereof to a cell binding agent.

The term "precursor" of a given group refers to any group which may lead to that group by any deprotection, a chemical modification, or a coupling reaction.

The term "linked to a cell binding agent" refers to a conjugate molecule comprising at least one of the compounds described herein (e.g., compounds of formula (I) or (II)), or derivative thereof bound to a cell binding agent via a suitable linking group or a precursor thereof.

The term "chiral" refers to molecules which have the property of non-superimposability of the mirror image partner, while the term "achiral" refers to molecules which are superimposable on their minor image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not minor images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable minor images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are minor images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, .beta.-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "prodrug" is also meant to include a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, .alpha.-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines. Particularly favored prodrugs and prodrug salts are those that increase the bioavailability of the compounds of this invention when such compounds are administered to a mammal.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Further-more, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound which further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The term "cytotoxic agent" as used herein refers to any compound that results in the death of a cell, induces cell death, or decreases cell viability. Suitable cytotoxic agents include, for example, maytansinoids and maytansinoid analogs, taxoids, CC-1065 and CC-1065 analogs, and dolastatin and dolastatin analogs. In a preferred embodiment of the invention, the cytotoxic agent is a maytansinoid, including maytansinol, maytansinol analogs, ansamitocin and ansamitocin analogs. Maytansinoids are compounds that inhibit microtubule formation and are highly toxic to mammalian cells. Examples of suitable maytansinol analogues include those having a modified aromatic ring and those having modifications at other positions. Such maytansinoids are described in, for example, U.S. Pat. Nos. 4,256,746, 4,294, 757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

Examples of maytansinol analogs having a modified aromatic ring include: (1) C-19-dechloro (U.S. Pat. No. 4,256,746) (prepared by LAH reduction of ansamytocin P2), (2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH), and (3) C-20-demethoxy, C-20-acyloxy (—OCOR), +/−dechloro (U.S. Pat. No. 4,294,757) (prepared by acylation using acyl chlorides).

Examples of maytansinol analogs having modifications of positions other than an aromatic ring include: (1) C-9-SH (U.S. Pat. No. 4,424,219) (prepared by the reaction of maytansinol with $H_2S$ or $P_2S_5$), (2) C-14-alkoxymethyl (demethoxy/$CH_2OR$) (U.S. Pat. No. 4,331,598), (3) C-14-hydroxymethyl or acyloxymethyl ($CH_2OH$ or $CH_2OAc$) (U.S. Pat. No. 4,450,254) (prepared from *Nocardia*), (4) C-15-hydroxy/acyloxy (U.S. Pat. No. 4,364,866) (prepared by the conversion of maytansinol by *Streptomyces*), (5) C-15-methoxy (U.S. Pat. Nos. 4,313,946 and 4,315,929) (isolated from *Trewia nudiflora*), (6) C-18-N-demethyl (U.S. Pat. Nos. 4,362,663 and 4,322,348) (prepared by the demethylation of maytansinol by *Streptomyces*), and (7) 4,5-deoxy (U.S. Pat. No. 4,371,533) (prepared by the titanium trichloride/LAH reduction of maytansinol).

The terms "abnormal cell growth" and "proliferative disorder" are used interchangeably in this application. "Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, as well as head/brain and neck cancer.

A "therapeutic agent" encompasses both a biological agent such as an antibody, a peptide, a protein, an enzyme or a chemotherapeutic agent.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)qu-inazoline (ZD6474; Example 2 within WO 01/32651), 4-(4-fluoro-2-methylindol-5-yloxy)-6-methoxy-7-(3-pyrrolidin-1-ylpropoxy)-1-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds include inhibitors of PI3K (phosphoinositide-3 kinase), such as those reported in Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

A "metabolite" is a product produced through metabolism in the body of a specified compound, a derivative thereof, or a conjugate thereof, or salt thereof. Metabolites of a compound, a derivative thereof, or a conjugate thereof, may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

A "linking group" as defined herein refers to a functional group that can form a chemical bond with a cell-binding agent. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. In one embodiment, the linking group is selected from the group consisting of a maleimide, a haloacetamido, —SH, —SSR$^f$, —CH$_2$SH, —CH(Me)SH, —C(Me)$_2$SH, —NHR$^g$, —CH$_2$NHR$^g$, —NR$^g$NH$_2$, —COOH, a reactive ester, an amino acid, or a peptide having 2 to 10 amino acids, wherein R$^f$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl) and R$^g$ is —H or a C$_{1-4}$ alkyl.

The term "linking moiety" as used herein refers to the remaining chemical moiety of the linking group after the linking group is covalently linked to a cell-binding agent. For example, when the linking group N-hydroxysuccinimide ester is chemically linked with an amine group of the cell-binding agent, the corresponding linking moiety is —C(=O)—. In another example, when the linking group maleimide group is chemically linked to a thio (—SH) group of the cell-binding agent, the linking moiety is

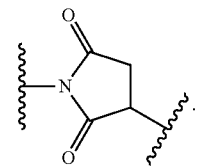 [SMILES: *C1CC(=O)N(*)C1=O]

The "reactive ester" as used herein refers to an ester group having a leaving group that is readily displaced by an amine or a hydroxyl group. Examples of a reactive ester, include, but are not limited to, N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetraflurophenyl (e.g., 4-sulfo-2,3,5,6-tetrafluorophenyl)ester and pentafluorophenyl ester.

As used herein, a "bifunctional crosslinking reagent" refers to a reagent that possesses two reactive groups; one of which is capable of reacting with a cell-binding agent while the other one reacts with the cytotoxic compound D-XH to link the two moieties together. Such bifunctional crosslinkers are well known in the art (see, for example, Isalm and Dent in *Bioconjugation* chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups. Other bifunctional crosslinking agents that introduce maleimido groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), N-(α-maleimidoacetoxy)-succinimide ester (AMAS), κ-maleimidoundecanoic acid N-succinimidyl ester (KMUA), N-(β-maleimidopropyloxy)succinimide ester (BMPS), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP), succinimidyl-(4-vinylsulfonyl)benzoate (SBSV), bis-maleimidopolyethyleneglycol (BMPEO), BM(PEO)$_2$, BM(PEO)$_3$, 5-maleimidovaleric acid NHS, HBVS, 4-(4-N-maleimidophenyl)-butyric acid hydrazide.HCl (MPBH), Succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl) aminobenzoate (sulfo-S TAB), m-Maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-κ-maleimidoundecanoyloxy)sulfosuccinimide ester (sulfo-KMUS), sulfosuccinimidyl 4-(p-maleimidophenyl)butyrate (sulfo-SMPB), CX1-1, sulfo-Mal and PEG$_n$-Mal. Preferably, the bifunctional crosslinking reagent is SMCC.

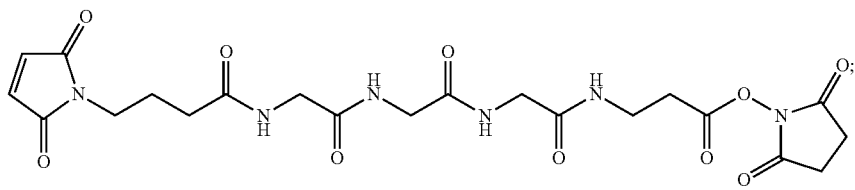

(CX1-1)

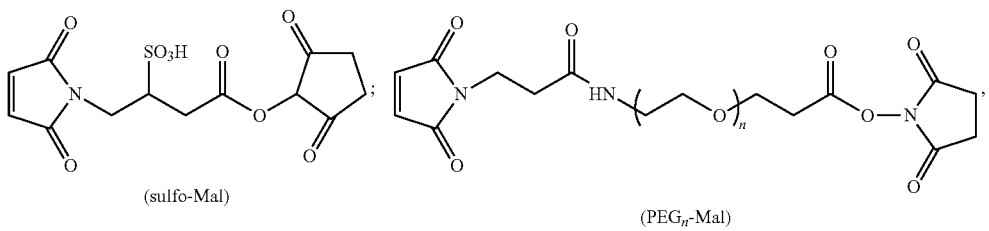

(sulfo-Mal)      (PEG$_n$-Mal)

wherein n is 2 to 24. Preferably, for PEG$_n$-Mal, n is 2 to 10.

More preferably, n is 2, 4, 6 or 8.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

Cytotoxic Compounds

The present invention is directed to cytotoxic compounds (e.g., compounds of structural formulas(I'), (I) and (II)) and conjugates (e.g., conjugates represented by structural formula (III'), (III) or (IV)) described herein.

In one embodiment, for structural formulas (I'), (I), (II), (III'), (III) or (IV), the definitions for the variables depicted therein are as defined below:

1. D in structural formulas (I'), (I), (II), (III'), (III) or (IV) is a cytotoxic agent. In a preferred embodiment, D is a maytansinoid. In a more preferred embodiment, D is represented by the following structural formula:

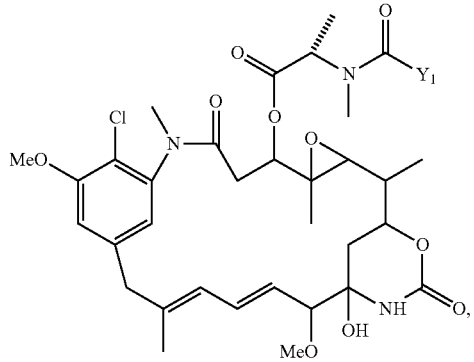

(A1)

wherein:

$Y_1$ represents $(CR_7R_8)_l(CR_5R_6)_m(CR_3R_4)_nCR_1R_2$—, $R_1, R_2, R_3, R_4, R_5, R_6, R_7$ and $R_8$ are each independently H, an alkyl, an alkenyl, a cycloalkyl, a heteroaryl, a heterocyclyl, or an aryl; and l, m and n are each independently 0 or an integer from 1 to 5.

In another preferred embodiment, D is represented by structural formula (A1), wherein $R_1$ and $R_2$ are each independently H, $C_{1-4}$ alkyl or $C_{1-4}$ alkyl substituted with one to six halogens. More preferably, $R_1$ and $R_2$ are each independently H, methyl, —$CF_3$ or —$CCl_3$. Even more preferably, $R_1$ and $R_2$ are both H or methyl.

In another preferred embodiment, D is represented by structural formula (A1), wherein l and m are 0, n is 1, $R_1, R_2, R_3$ and $R_4$ are all H.

In another preferred embodiment, D is represented by structural formula (A1), wherein n is 0, l and m are both 1, $R_5, R_6, R_7$ and $R_8$ are all H, $R_1$ and $R_2$ are both methyl.

In yet another preferred embodiment, D is represented by structural formula (A1), wherein n is 0, l and m are both 1, $R_1, R_5, R_6, R_7$ and $R_8$ are all H, and $R_2$ is methyl 2. X in structural formulas (I), (II), (III) and (IV) is S or Se. In one embodiment, X is S. In another embodiment, X is Se.

3. R and R' in structural formulas (I) and (III) are each independently selected from the group consisting of —H, an alkyl, a cycloalkyl, —$OR^a$, and —$NR^bR^c$, wherein $R^a$, $R^b$ and $R^c$ are each independently H or an alkyl. Preferably, one of R and R' is H, and the other is H, a $C_{1-4}$ alkyl, —$OR^a$ or —$NR^bR^c$, wherein $R^a$, $R^b$ and $R^c$ are each independently H or $C_{1-4}$ alkyl. More preferably, R and R' are both H.

4. p in structural formulas (I) and (III) is 0, 1 or 2. Preferably, p is 0.

5. Y" in structural formulas (I') and (III') is a spacer. In one embodiment, when p is 0, —Y"M is the non-maleimide moiety of a maleimide-containing bifunctional crosslinking reagent. In another embodiment, Y" is an alkylene, a polyethylene glycol unit represented by —($CH_2$—$CH_2$—O)$_n$—$R^d$—, —$R^d$-E- or —$R^d$—W—$R^{e'}$—, wherein:

n is an integer from 1 to 24;

E is a cycloalkyl, a heterocyclyl, an aryl or a heteroaryl,

W is —C(=O)NH—, —NHC(=O)—, —(C=O)O— or —O(C=O)—, $R^d$ is absent or an alkyl; and $R^{e'}$ is an alkyl or a polyethylene glycol unit represented by —($CH_2$—$CH_2$—O)$_n$—$R^d$—.

In one embodiment, Y in structural formulas (I) and (III) is an alkylene, a polyethylene glycol unit represented by —($CH_2$—$CH_2$—O)$_n$—$R^d$—, —$R^d$-E- or —$R^d$—W—$R^e$—, wherein:

n is an integer from 1 to 24;

E is a cycloalkyl, a heterocyclyl, an aryl or a heteroaryl,

W is —C(=O)NH—, —NHC(=O)—, —(C=O)O— or —O(C=O)—, $R^d$ is absent or an alkyl; and $R^e$ is an alkyl.

Preferably, Y is a $C_{1-6}$ alkylene, a polyethylene glycol unit represented by —($CH_2$—$CH_2$—O)$_n$—$R^d$—, —$R^d$-E- or —$R^d$—W—$R^e$—, wherein $R^d$ is absent or a $C_{1-4}$ alkyl; $R^e$ is a $C_{1-4}$ alkyl; W is —C(=O)NH—; E is cyclohexyl and n is an integer from 2 to 8.

In another preferred embodiment, Y is

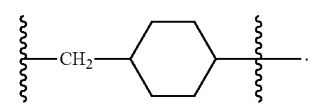

5. M in structural formula (I'), (I) and (II) is a linking group that can react with a cell-binding agent to form a covalent bond. Preferably, M is a maleimide, a haloacetamido, —SH, —$SSR^f$, —$CH_2SH$, —CH(Me)SH, —C(Me)$_2$ SH, —NHR$^g$, —CH$_2$NHR$^g$, —NR$^g$NH$_2$, —COOH, a reactive ester, an amino acid or a peptide comprising 2 to 10 amino acids, wherein R$^f$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl) and R$^g$ is —H or a C$_{1-4}$ alkyl.

In a preferred embodiment, M is a maleimide, haloacetamido, N-hydroxysuccinimde ester, N-hydroxy sulfosuccinimide ester, nitrophenyl (e.g., 2 or 4-nitrophenyl)ester, dinitrophenyl (e.g., 2,4-dinitrophenyl) ester, sulfotetrafluorophenyl (e.g., 4-sulfo-2,3,5,6-tetrafluorophenyl) ester or pentafluorophenyl ester. More preferably, M is N-hydroxysuccinimide ester.

6. M' in structural formulas (III'), (III) and (IV) is a linking moiety that covalently linked to the cell-binding agent. Preferably, M' is —C(=O)—,

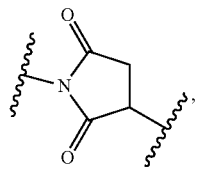 [SMILES: *C1CC(=O)N(*)C1=O]

—NH—C(=O)—CH$_2$—, —S—, —CH$_2$—S—, —CH(Me)-S—, —C(Me$_2$)-S—, —NR$^g$—, —CH$_2$NR$^g$—, or —NR$^g$N=, wherein R$^g$ is —H or a C$_{1-4}$ alkyl. More preferably, M' is —C(=O)—.

7. For structural formulas (II) and (IV), Y' is —SO$_2$—, aryl, pyridyl or —C(=)—; Z is an alkyl, a cycloalkyl, a heterocyclyl, an aryl, a heteroaryl, or —N(R$^b$)—R$^d$—; wherein R$^b$ is H or a C$_{1-4}$ alkyl; and R$^d$ is a C$_{1-4}$ alkyl.

In a preferred embodiment, Y' is —SO$_2$—; and Z is optionally substituted phenyl. More preferably, Z is unsubstituted phenyl.

In another preferred embodiment, Y' is phenyl or pyridyl, more preferably, Y' is pyridyl and Y' is linked with Z through the pyridyl nitrogen atom. Z is an alkyl. Preferably, Z is a C$_{1-4}$ alkyl.

In yet another preferred embodiment, Y' is —C(=O)—, and Z is —N(R$^b$)—R$^d$—, wherein R$^b$ is H and R$^d$ is —CH$_2$—CH$_2$—.

In a first embodiment, the present invention is directed to a compound of structural formula (I') or (I):

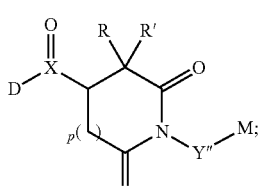

(I')

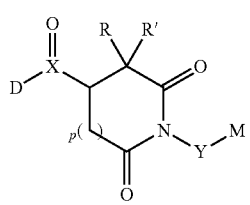

(I)

wherein the definitions for each variable are described above.

In a second embodiment, for the compound of structural formula (I') or (I):

D is represented by structural formula (A1):

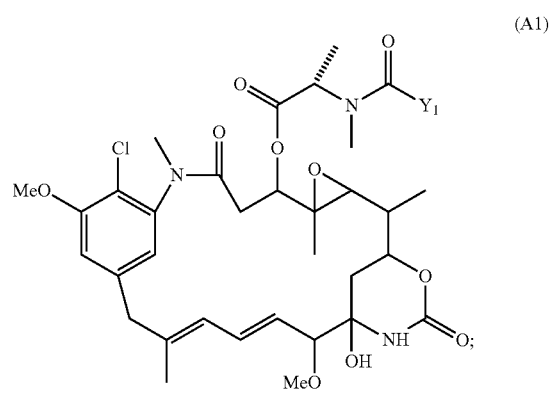

(A1)

Y$_1$ represents (CR$_7$R$_8$)$_l$(CR$_5$R$_6$)$_m$(CR$_3$R$_4$)$_n$CR$_1$R$_2$—, R$_1$, R$_2$, R$_3$, R$_4$, R$_5$, R$_6$, R$_7$ and R$_8$ are each independently H, an alkyl, an alkenyl, a cycloalkyl, a heteroaryl, a heterocyclyl, or an aryl; and l, m and n are each independently 0 or an integer from 1 to 5;

p is 0;

X is S; and the remainder of the variables are as described above for structural formula (I).

In a third embodiment, for compound of structural formula (I') or (I):

D is represented by structural formula (A2):

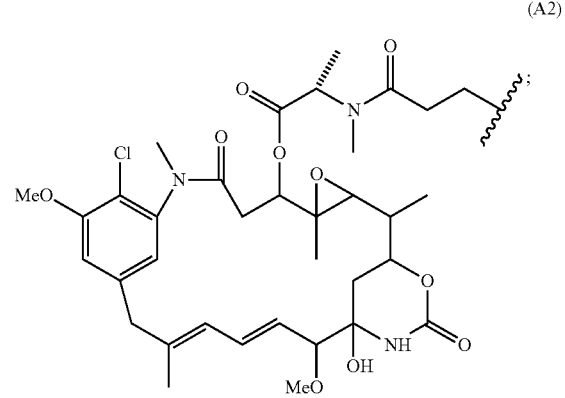 [SMILES: *CCC(=O)N(C)[C@@H](C)C(=O)OC1CC(=O)N(C)c2cc(cc(OC)c2Cl)C/C(C)=C/C=C/C(OC)C2(O)CC(OC(=O)N2)C(C)C2OC12C]

(A2)

p is 0;

X is S; and the remainder of the variables are as described above for structural formula (I).

In a fourth embodiment, for compound of structural formula (I') or (I):

D is represented by structural formula (A3):

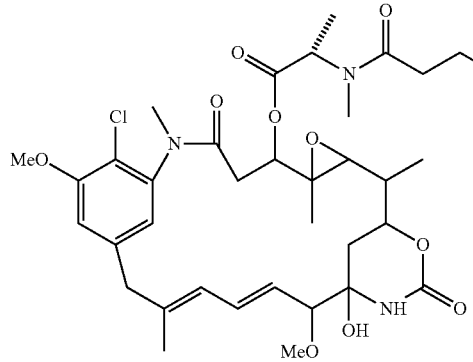

p is 0;

X is S; and the remainder of the variables are as described above for structural formula (I).

In a fifth embodiment, for compound of structural formula (I') described in the second, third or fourth embodiment, when p is 0, —Y"M is the non-maleimide moiety of a maleimide-containing bifunctional crosslinking reagent. In another embodiment, for compound of structural formula (I'), Y" is an alkylene, a polyethylene glycol unit represented by —(CH$_2$—CH$_2$—O)$_n$—R$^d$—, —R$^d$-E- or —R$^d$—W—R$^{e_1}$—, wherein:

n is an integer from 1 to 24;

E is a cycloalkyl, a heterocyclyl, an aryl or a heteroaryl,

W is —C(=O)NH—, —NHC(=O)—, —(C=O)O— or —O(C=O)—,

R$^d$ is absent or an alkyl; and

R$^{e_1}$ is an alkyl or —(CH$_2$—CH$_2$—O)$_n$—R$^d$—.

Preferably, Y" is —R$^d$—W—R$^{e_1}$—, wherein R$^d$ is a C$_{1-4}$ alkyl, W is —C(=O)NH— or —NHC(=O)—, and R$^{e_1}$ is —(CH$_2$—CH$_2$—O)$_n$—R$^d$—. Even more preferably, n is an integer from 2 to 10.

In another embodiment, for compound of structural formula (I) described in the second, third or fourth embodiment:

Y is a C$_{1-6}$ alkylene, a polyethylene glycol unit represented by —(CH$_2$—CH$_2$—O)$_n$—R$^d$—, —R$^d$-E- or —R$^d$—W—R$^{e}$—, wherein R$^d$ is absent or a C$_{1-4}$ alkyl; R$^e$ is a C$_{1-4}$ alkyl; W is —C(=O)NH—; E is cyclohexyl and n is an integer from 2 to 8; and M is a maleimide, a haloacetamido, —SH, —SSR$^f$, —CH$_2$SH, —CH(Me)SH, —C(Me)$_2$SH, —NHR$^g$, —CH$_2$NHR$^g$, —NR$^g$NH$_2$, —COOH, a reactive ester, an amino acid, a peptide comprising 2 to 10 amino acids, wherein R$^f$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl) and R$^g$ is —H or a C$_{1-4}$ alkyl.

Preferably, Y is

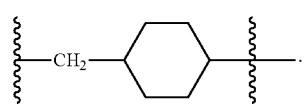

Even more preferably, Y is

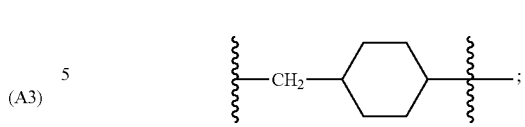

and M is N-hydroxysuccinimide ester.

In a sixth embodiment, the present invention is directed to a compound represented by structural formula (II):

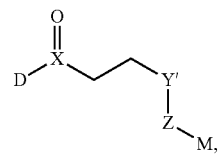

wherein the variables are as described above for structural formula (II).

In a seventh embodiment, for compound of structural formula (II):

D is represented by structural formula (A1):

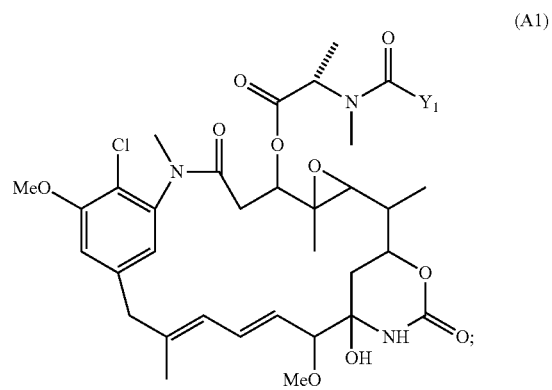

Y$_1$ represents (CR$_7$R$_8$)$_l$(CR$_5$R$_6$)$_m$(CR$_3$R$_4$)$_n$CR$_1$R$_2$—, R$_1$, R$_2$, R$_3$, R$_4$, R$_5$, R$_6$, R$_7$ and R$_8$ are each independently H, an alkyl, an alkenyl, a cycloalkyl, a heteroaryl, a heterocyclyl, or an aryl;

l, m and n are each independently 0 or an integer from 1 to 5;

X is S; and the remainder of the variables are as described in structural formula (II).

In a preferred embodiment, Y' is SO$_2$ and Z is an optionally substituted phenyl. The remainder of the variables is as described above in the seventh embodiment. More preferably, Z is an unsubstituted phenyl.

In another preferred embodiment, Y' is pyridyl or phenyl; Z is an alkyl; more preferably, Y' is pyridyl and Y' is linked with Z through the pyridyl nitrogen. The remainder of the variables is as described above in the seventh embodiment. More preferably, Z is a C$_{1-4}$ alkyl.

In another preferred embodiment, Y' is —C(=O)—; and Z is —N(R$^b$)—R$^d$—, wherein R$^b$ is H or an alkyl; and R$^d$ is an alkyl. The remainder of the variables is as described above in the seventh embodiment. More preferably, R$^b$ is H and R$^d$ is a C$_{1-4}$ alkyl. Even more preferably, R$^b$ is H and R$^d$ is —CH$_2$—CH$_2$—.

In a eighth embodiment, for compound of structural formula (II):

D is represented by structural formula (A2):

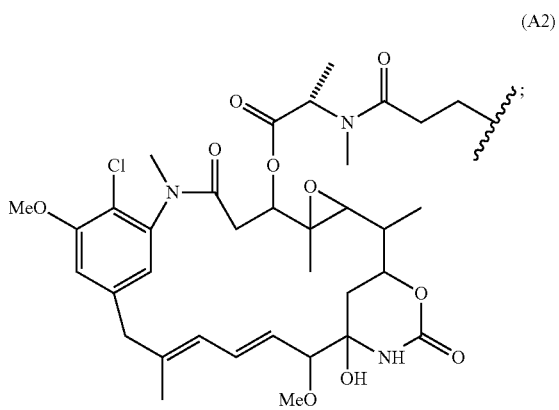 [SMILES: *CCC(=O)N(C)[C@@H](C)C(=O)OC1CC(=O)N(C)c2cc(cc(OC)c2Cl)C/C(C)=C/C=C/C(OC)C2(O)CC(OC(=O)N2)C(C)C2OC12C]

X is S; and the remainder of the variables are as described in structural formula (II).

In a preferred embodiment, Y' is $SO_2$ and Z is an optionally substituted phenyl. The remainder of the variables is as described above in the eighth embodiment. More preferably, Z is an unsubstituted phenyl.

In another preferred embodiment, Y' is phenyl or pyridyl; Z is an alkyl; more preferably, Y' is pyridyl and Y' is linked with Z through the pyridyl nitrogen. The remainder of the variables is as described above in the eighth embodiment. More preferably, Z is a $C_{1-4}$ alkyl.

In another preferred embodiment, Y' is —C(=O)—; and Z is —N($R^b$)—$R^d$—, wherein $R^b$ is H or an alkyl; and $R^d$ is an alkyl. The remainder of the variables is as described above in the eighth embodiment. More preferably, $R^b$ is H and $R^d$ is a $C_{1-4}$ alkyl. Even more preferably, $R^b$ is H and $R^d$ is —$CH_2$—$CH_2$—.

In a ninth embodiment, for compound of structural formula (II):

D is represented by structural formula (A3):

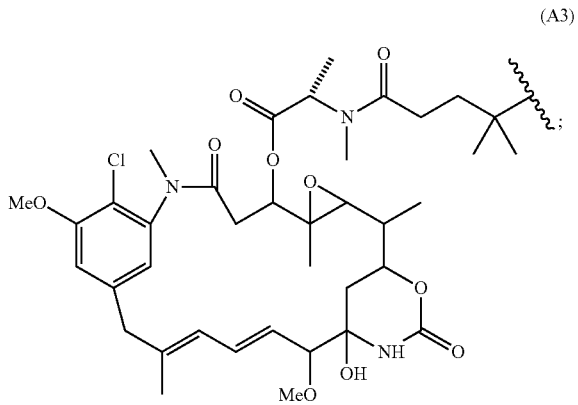 [SMILES: *C(C)(C)CCC(=O)N(C)[C@@H](C)C(=O)OC1CC(=O)N(C)c2cc(cc(OC)c2Cl)C/C(C)=C/C=C/C(OC)C2(O)CC(OC(=O)N2)C(C)C2OC12C]

X is S; and the remainder of the variables are as described in structural formula (II).

In a preferred embodiment, Y' is $SO_2$ and Z is an optionally substituted phenyl. The remainder of the variables is as described above in the ninth embodiment. More preferably, Z is an unsubstituted phenyl.

In another preferred embodiment, Y' is phenyl or pyridyl; Z is an alkyl; and more preferably, Y' is pyridyl and Y' is linked with Z through the pyridyl nitrogen. The remainder of the variables is as described above in the ninth embodiment. More preferably, Z is a $C_{1-4}$ alkyl.

In another preferred embodiment, Y' is —C(=O)—; and Z is —N($R^b$)—$R^d$—, wherein $R^b$ is H or an alkyl; and $R^d$ is an alkyl. The remainder of the variables is as described above in the ninth embodiment. More preferably, $R^b$ is H and $R^d$ is a $C_{1-4}$ alkyl. Even more preferably, $R^b$ is H and $R^d$ is —$CH_2$—$CH_2$—.

Cell-Binding Agents

The effectiveness of the conjugates of the invention as therapeutic agents depends on the careful selection of an appropriate cell-binding agent. Cell-binding agents may be of any kind presently known, or that become known and includes peptides and non-peptides. Generally, these can be antibodies (especially monoclonal antibodies), lymphokines, hormones, growth factors, vitamins, nutrient-transport molecules (such as transferrin), or any other cell-binding molecule or substance.

More specific examples of cell-binding agents that can be used include:

polyclonal antibodies;

monoclonal antibodies;

fragments of antibodies such as Fab, Fab', and F(ab')$_2$, Fv, minibodies, diabodies, tribodies, tetrabodies, nanobodies, probodies, domain bodies, unibodies and the like (Parham, *J. Immunol.* 131:2895-2902 (1983); Spring et al. *J. Immunol.* 113:470-478 (1974); Nisonoff et al. *Arch. Biochem. Biophys.* 89:230-244 (1960), Kim et al., Mol, Cancer Ther., 7: 2486-2497 (2008), Carter, Nature Revs., 6: 343-357 (2006), R. Kontermann & S. Dubel, 2001 Antibody Engineering, Springer-Verlag, Heidelberg-New York);

bispecific antibodies (Morrison, S L *Nature biotechnology* 25 (11): 1233-4 (2007));

ankyrin repeat proteins (DARPins; Zahnd et al., *J. Biol. Chem.*, 281, 46, 35167-35175, (2006); Binz, H. K., Amstutz, P. & Pluckthun, A. (2005) *Nature Biotechnology*, 23, 1257-1268) or ankyrin-like repeats proteins or synthetic peptides described, for example, in U.S. Patent Publication Number 20070238667; U.S. Pat. No. 7,101,675; and WO/2007/147213; WO/2007/062466)

interferons (e.g. .alpha., .beta., .gamma.);

lymphokines such as IL-2, IL-3, IL-4, IL-6;

hormones such as insulin, TRH (thyrotropin releasing hormone), MSH (melanocyte-stimulating hormone), steroid hormones, such as androgens and estrogens;

growth factors and colony-stimulating factors such as EGF, TGF-alpha, FGF, VEGF, G-CSF, M-CSF and GM-CSF (Burgess, *Immunology Today* 5:155-158 (1984));

transferrin (O'Keefe et al. *J. Biol. Chem.* 260:932-937 (1985)); and vitamins, such as folate.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047;

Liming et al., WO 99/06587). In addition, resurfaced antibodies disclosed in U.S. Pat. No. 5,639,641 may also be used, as may chimeric antibodies and humanized antibodies. Selection of the appropriate cell-binding agent is a matter of choice that depends upon the particular cell population that is to be targeted, but in general human monoclonal antibodies are preferred if an appropriate one is available.

For example, the monoclonal antibody MY9 is a murine IgG$_1$ antibody that binds specifically to the CD33 Antigen {J. D. Griffin et al 8 Leukemia Res., 521 (1984)} and can be used if the target cells express CD33 as in the disease of acute myelogenous leukemia (AML). The cell-binding agent may be any compound that can bind a cell, either in a specific or non-specific manner. Generally, these can be antibodies (especially monoclonal antibodies and antibody fragments), interferons, lymphokines, hormones, growth factors, vitamins, nutrient-transport molecules (such as transferrin), or any other cell-binding molecule or substance.

Where the cell-binding agent is an antibody, it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, EpCAM, GD3, FLT3, PSMA, PSCA, MUC1, MUC16, STEAP, CEA, TENB2, EphA receptors, EphB receptors, folate receptor, FOLR1, mesothelin, cripto, alpha$_v$beta$_6$, integrins, VEGF, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in US Publication No. 20080171040 or US Publication No. 20080305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; endoglin, c-Met, 1GF1R, PSGR, NGEP, PSMA, PSCA, LGR5, B7H4, TAG72 (tumor-associated glycoprotein 72), and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

In one embodiment, the antibody is selected from the group consisting of huN901, huMy9-6, huB4, huC242, trastuzumab, bivatuzumab, sibrotuzumab, rituximab, huDS6, anti-mesothelin antibodies described in WO 2010/124797 (such as MF-T), anti-cripto antibodies described in US Patent Application Publication 2010/0093980 (such as huB3F6), anti-CD138 antibodies described in US Patent Application Publication 2007/0183971 (such as huB-B4), anti-EGFRvIII antibodies described U.S. Pat. Nos. 7,736,644 and 7,628,986 and US Application Publication Nos. 2010/0111979, 2009/0240038, 2009/0175887, 2009/0156790 and 2009/0155282, humanized EphA2 antibodies described in PCT/IB2010/054417 and PCT/IB2010/054422 (such as 2H11R35R74); anti-CD38 antibodies described in WO2008/047242 (such as hu38SB19), anti-folate receptor antibodies described in U.S. Provisional Application Nos. 61/307,797, 61/346,595 and 61/413,172, and U.S. application Ser. No. 13/033,723 (e.g., huMov19); anti-IGF1R antibodies described in U.S. Pat. Nos. 5,958,872 and 6,596,743; anti-CD37 antibodies described in U.S. application Ser. No. 13/045,693, filed on Mar. 11, 2011 (e.g., huCD37-3); anti-integrin α$_v$β$_6$ antibodies described in U.S. Application Publication No. 2006/0127407 (e.g., CNTO95); and anti-Her3 antibodies described in U.S. Provisional Application Nos. 61/370,701.

Particularly preferred antibodies are humanized monoclonal antibodies described herein. Examples include, but are not limited to, huN901, huMy9-6, huB4, huC242, trastuzumab, bivatuzumab, sibrotuzumab, CNTO95, huDS6, and rituximab (see, e.g., U.S. Pat. Nos. 5,639,641 and 5,665,357, U.S. Provisional Patent Application No. 60/424,332 (which is related to U.S. Pat. No. 7,557,189), International (PCT) Patent Application Publication WO 02/16401, Pedersen et al., supra, Roguska et al., supra, Liu et al., supra, Nadler et al., supra, Colomer et al., *Cancer Invest.*, 19: 49-56 (2001), Heider et al., *Eur. J. Cancer,* 31A: 2385-2391 (1995), Welt et al., *J. Clin. Oncol.,* 12: 1193-1203 (1994), and Maloney et al., *Blood,* 90: 2188-2195 (1997)). Other humanized monoclonal antibodies are known in the art and can be used in connection with the invention.

In one embodiment, the anti-folate antibody is a humanized antibody or antigen binding fragment thereof that specifically binds a human folate receptor 1, wherein the antibody comprises: (a) a heavy chain CDR1 comprising GYFMN (SEQ ID NO:5); a heavy chain CDR2 comprising RIHPYDGDTFYNQXaa$_1$FXaa$_2$Xaa$_3$ (SEQ ID NO:6); and a heavy chain CDR3 comprising YDGSRAMDY (SEQ ID NO:7); and (b) a light chain CDR1 comprising KASQS-VSFAGTSLMH (SEQ ID NO:8); a light chain CDR2 comprising RASNLEA (SEQ ID NO:9); and a light chain CDR3 comprising QQSREYPYT (SEQ ID NO:10); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG (SEQ ID NO:11).

In another embodiment, the anti-folate receptor antibody is a humanized antibody or antigen binding fragment thereof that specifically binds the human folate receptor 1 comprising the heavy chain having the amino acid sequence of QVQLVQSGAEVVKPGASVKISCKASGYTFTGYFMN-WVKQSPGQSLEWIGRIHPYDGDT FYNQKFQG-KATLTVDKSSNTAHMELLSLTSEDFAVYYCTRYDG-SRAMDYWGQGTTVT VSSASTKGPSVFPLAPSSKSTSGGTAALGCLVKDYF-PEPVTVSWNSGALTSGVHTFPAVL QSSGLYSLSSVVT-VPSSSLGTQTYICNVNHKPSNTKVDKKVEPKSCDK-THTCPPCPAPEL LGGPSVFLFPPKPKDTLMISRTPEVTCVVVDVSHED-PEVKFNWYVDGVEVHNAKTKPRE EQYNSTYRVVS-VLTVLHQDWLNGKEYKCKVSNKALPAPIEKTISKAK-GQPREPQVYTLP PSRDELTKNQVSLTCLVKGFYPSDIAVEW-ESNGQPENNYKTTPPVLDSDGSFFLYSKLTV DKSR-WQQGNVFSCSVMHEALHNHYTQKSLSLSPGK (SEQ ID NO:1).

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof comprising a heavy chain variable domain at least about 90%, 95%, 99% or 100% identical to QVQLVQSGAEVVKPGASVKISCKASGYTFTGYFMN-WVKQSPGQSLEWIGRIHPYDGDT FYNQKFQG-KATLTVDKSSNTAHMELLSLTSEDFAVYYCTRYDG-SRAMDYWGQGTTVT VSS (SEQ ID NO:2), and a light chain variable domain at least about 90%, 95%, 99% or 100% identical to DIVLTQSPLSLAVSLGQPAIISCKASQSVSFAGTSLMH-WYHQKPGQQPRLLIYRASNLEA GVPDRFSGSGSK-TDFTLNISPVEAEDAATYYCQQSREYPYTFGGGT-KLEIKR (SEQ ID N; or DIVLTQSPLSLAVSLGQPAIISCKASQSVSFAGTSLMH-WYHQKPGQQPRLLIYRASNLEA GVPDRFSGSGSK-TDFTLTISPVEAEDAATYYCQQSREYPYTFGGGT-KLEIKR (SEQ ID NO:4).

Cell-Binding Agent-Cytotoxic Compound Conjugates

The present invention also provides cell-binding agent-cytotoxic compound conjugates comprising a cell-binding agent linked to one or more cytotoxic compounds of the present invention via a variety of linkers, including, but not limited to, disulfide linkers, thioether linkers, amide bonded linkers, peptidase-labile linkers, acid-labile linkers, esterase-labile linkers. Representative conjugates of the invention are antibody/cytotoxic compound, antibody fragment/cytotoxic compound, epidermal growth factor (EGF)/cytotoxic compound, melanocyte stimulating hormone (MSH)/cytotoxic compound, thyroid stimulating hormone (TSH)/cytotoxic compound, somatostatin/cytotoxic compound, folate/cytotoxic compound, estrogen/cytotoxic compound, estrogen analogue/cytotoxic compound, androgen/cytotoxic compound, and androgen analogue/cytotoxic compound.

In one embodiment, the present invention provides conjugates comprising a cell-binding agent chemically linked to a compound of the present invention (e.g., compounds of formula (I'), (I) or (II)).

In one embodiment, the cell-binding agent can linked to the compound through an amine group, a thio group or a carboxy group.

In a tenth embodiment, the present invention is directed to a conjugate represented by structural formula (III') or (III):

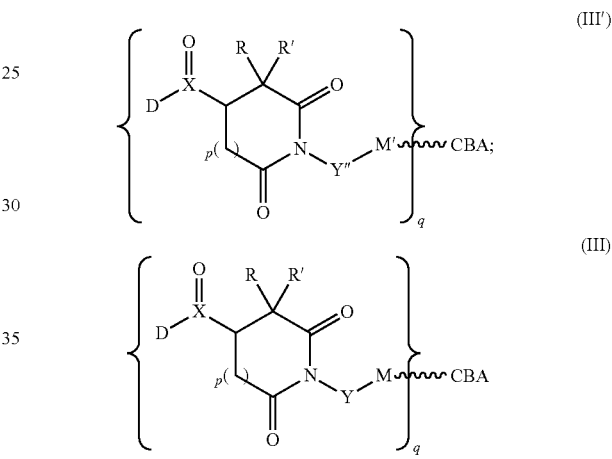

wherein values or preferred values for the variables are as described above for structural formula (III') or (III).

In a eleventh embodiment, for the conjugate of structural formula (III):

D is represented by structural formula (A1):

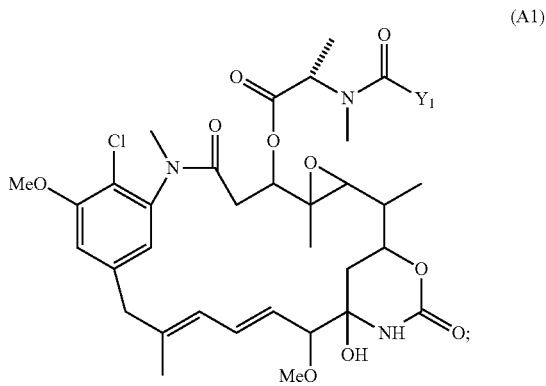

$Y_1$ represents $(CR_7R_8)_l(CR_5R_6)_m(CR_3R_4)_nCR_1R_2$—, $R_1$, $R_2$, $R_3$, $R_4$, $R_5$, $R_6$, $R_7$ and $R_8$ are each independently H, an alkyl, an alkenyl, a cycloalkyl, a heteroaryl, a heterocyclyl, or an aryl; and l, m and n are each independently 0 or an integer from 1 to 5;

p is 0;

X is S; and the remainder of the variables are as described above for structural formula (III).

In a twelfth embodiment, for the conjugate of structural formula (III):

D is represented by structural formula (A2):

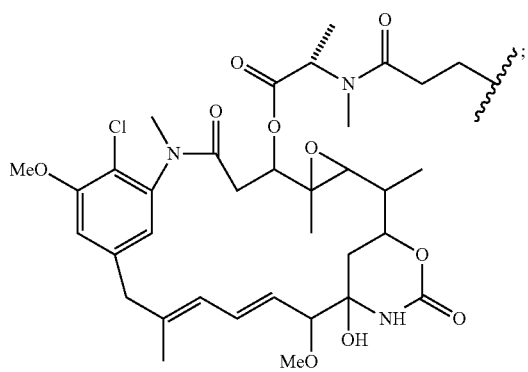

(A2)

p is 0;

X is S; and values and preferred values for the remainder of the variables is as described above for structural formula (III).

In a thirteen embodiment, for the conjugate of structural formula (III):

D is represented by structural formula (A3):

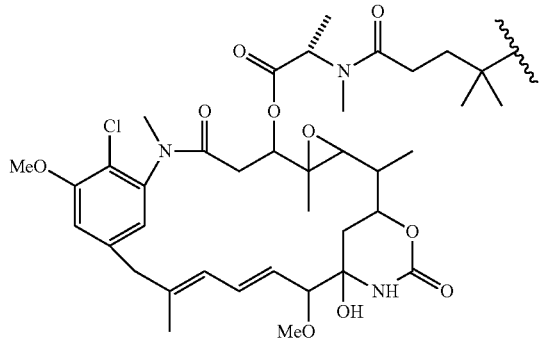

(A3)

p is 0;

X is S; and values and preferred values for the remainder of the variables are as described above for structural formula (III).

In a fourteenth embodiment, for conjugates of structural formula (III') in the eleventh, twelfth or thirteen embodiment, when p is 0, —Y"— is the non-maleimide and non-linking group moiety of a maleimide-containing bifunctional crosslinking reagent. In another embodiment, for compound of structural formula (III'), Y" is an alkylene, a polyethylene glycol unit represented by —(CH$_2$—CH$_2$—O)$_n$—R$^d$—, —R$^d$-E- or —R$^d$—W—$^{e1}$—, wherein:

n is an integer from 1 to 24;

E is a cycloalkyl, a heterocyclyl, an aryl or a heteroaryl;

W is —C(=O)NH—, —NHC(=O)—, —(C=O)O— or —O(C=O)—,

R$^d$ is absent or an alkyl; and

R$^{e1}$ is an alkyl or —(CH$_2$—CH$_2$—O)$_n$—R$^d$—.

Preferably, Y is —R$^d$—W—R$^{e1}$—, wherein R$^d$ is a C$_{1-4}$ alkyl, W is —C(=O)NH— or —NHC(=O)—, and R$^{e1}$ is —(CH$_2$—CH$_2$—O)$_n$—R$^d$—. Even more preferably, n is an integer from 2 to 10.

Even more preferably, Y" in structural formula (III') is represented by the following structural formula:

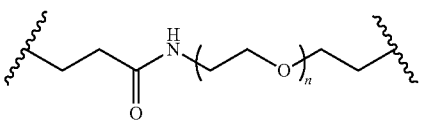

Preferably, n is an integer from 2 to 10. Even more preferably, n is 2, 4 or 8.

In another embodiment, for the conjugates of structural formula (III) described in the eleventh, twelfth or thirteen embodiment, Y is a C$_{1-6}$ alkylene, a polyethylene glycol unit represented by —(CH$_2$—CH$_2$—O)$_n$—R$^d$—, —R$^d$-E- or —R$^d$—W—R$^e$—, wherein R$^d$ is absent or a C$_{1-4}$ alkyl; R$^e$ is a C$_{1-4}$ alkyl; W is —C(=O)NH—; E is cyclohexyl and n is an integer from 2 to 8; and M' is —C(=O)—,

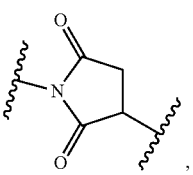 [SMILES: *C1CC(=O)N(*)C1=O]

—NH—C(=O)—CH$_2$—, —S—, —CH$_2$—S—, —CH(Me)-S—, —C(Me$_2$)-S—, —NR$^g$—, —CH$_2$NR$^g$—, or —NR$^g$N=, wherein R$^g$ is —H or a C$_{1-4}$ alkyl.

Preferably, Y is

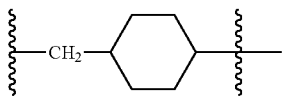

Even more preferably, Y is

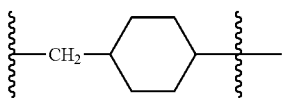

and M is —C(=O)—. Even more preferably, the CBA is linked to M through an amine (e.g. CBA-NH$_2$) group.

In a fifteenth embodiment, the present invention is directed to a conjugate represented by structural formula (IV):

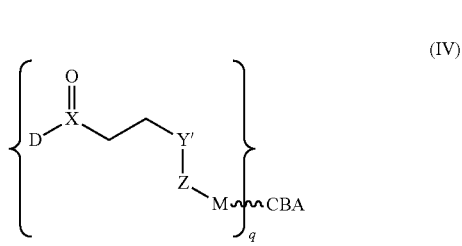

wherein the values and preferred values for the variables are as described above for structural formula (IV).

In a sixteenth embodiment, for the conjugate of structural formula (IV):

D is represented by structural formula (A1):

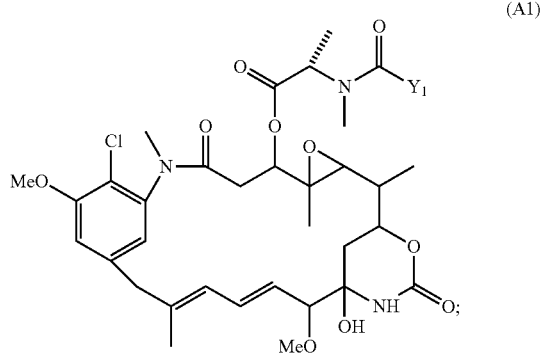

$Y_1$ represents $(CR_7R_8)_l(CR_5R_6)_m(CR_3R_4)_nCR_1R_2$—, $R_1$, $R_2$, $R_3$, $R_4$, $R_5$, $R_6$, $R_7$ and $R_8$ are each independently H, an alkyl, an alkenyl, a cycloalkyl, a heteroaryl, a heterocyclyl, or an aryl;

l, m and n are each independently 0 or an integer from 1 to 5;

X is S; and values and preferred values for the remainder of the variables is as described in structural formula (IV).

In a preferred embodiment, Y' is $SO_2$ and Z is an optionally substituted phenyl. The remainder of the variables is as described above in the sixteenth embodiment. More preferably, Z is an unsubstituted phenyl.

In another preferred embodiment, Y' is pheny or pyridyl; Z is an alkyl; and preferably, Y' is pyridyl and Y' is linked with Z through the pyridyl nitrogen. The remainder of the variables is as described above in the sixteenth embodiment. More preferably, Z is a $C_{1-4}$ alkyl.

In another preferred embodiment, Y' is —C(=O)—; and Z is —N($R^b$)—$R^d$—, wherein $R^b$ is H or an alkyl; and $R^d$ is an alkyl. The remainder of the variables is as described above in the sixteenth embodiment. More preferably, $R^b$ is H and $R^d$ is a $C_{1-4}$ alkyl. Even more preferably, $R^b$ is H and $R^d$ is —$CH_2$—$CH_2$—.

In a seventeenth embodiment, for the conjugates of structural formula (IV):

D is represented by structural formula (A2):

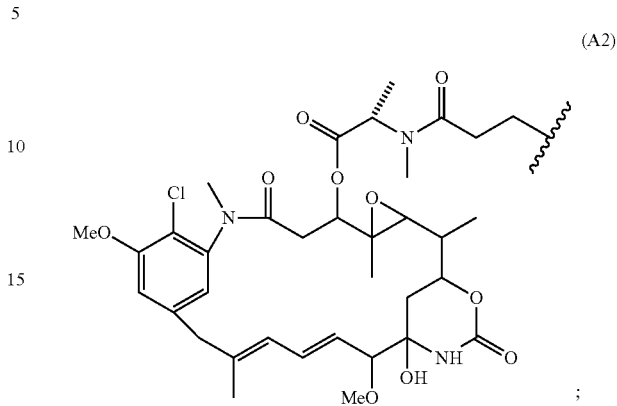

X is S; and values and preferred values for the remainder of the variables are as described in structural formula (II).

In a preferred embodiment, Y' is $SO_2$ and Z is an optionally substituted phenyl. The remainder of the variables is as described above in the seventeenth embodiment. More preferably, Z is an unsubstituted phenyl.

In another preferred embodiment, Y' is phenyl or pyridyl; Z is an alkyl; and more preferably, Y' is pyridyl and Y' is linked with Z through the pyridyl nitrogen. The remainder of the variables is as described above in the seventeenth embodiment. More preferably, Z is a $C_{1-4}$ alkyl.

In another preferred embodiment, Y' is —C(=O)—; and Z is —N($R^b$)—$R^d$—, wherein $R^b$ is H or an alkyl; and $R^d$ is an alkyl. The remainder of the variables is as described above in the seventeenth embodiment. More preferably, $R^b$ is H and $R^d$ is a $C_{1-4}$ alkyl. Even more preferably, $R^b$ is H and $R^d$ is —$CH_2$—$CH_2$—.

In a eighteenth embodiment, for the conjugates for formula (IV):

D is represented by structural formula (A3):

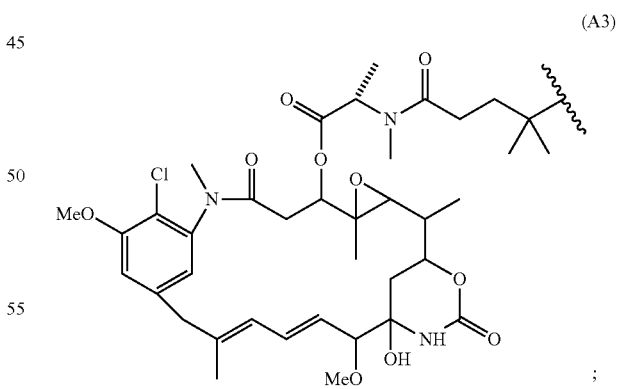

X is S; and values and preferred values for the remainder of the variables is as described in structural formula (II).

In a preferred embodiment, Y' is $SO_2$ and Z is an optionally substituted phenyl. The remainder of the variables is as described above in the eighteenth embodiment. More preferably, Z is an unsubstituted phenyl.

In another preferred embodiment, Y' is phenyl or pyridyl; Z is an alkyl; and more preferably, Y' is pyridyl and Y' is linked with Z through the pyridyl nitrogen. The remainder of the variables is as described above in the eighteenth embodiment. More preferably, Z is a $C_{1-4}$ alkyl.

In another preferred embodiment, Y' is —C(=O)—; and Z is —N($R^b$)—$R^d$—, wherein $R^b$ is H or an alkyl; and $R^d$ is an alkyl. The remainder of the variables is as described above in the eighteenth embodiment. More preferably, $R^b$ is H and $R^d$ is a $C_{1-4}$ alkyl. Even more preferably, $R^b$ is H and $R^d$ is —CH$_2$—CH$_2$—.

In a nineteenth embodiment, the conjugate of the present invention is represented by the following structural formula:

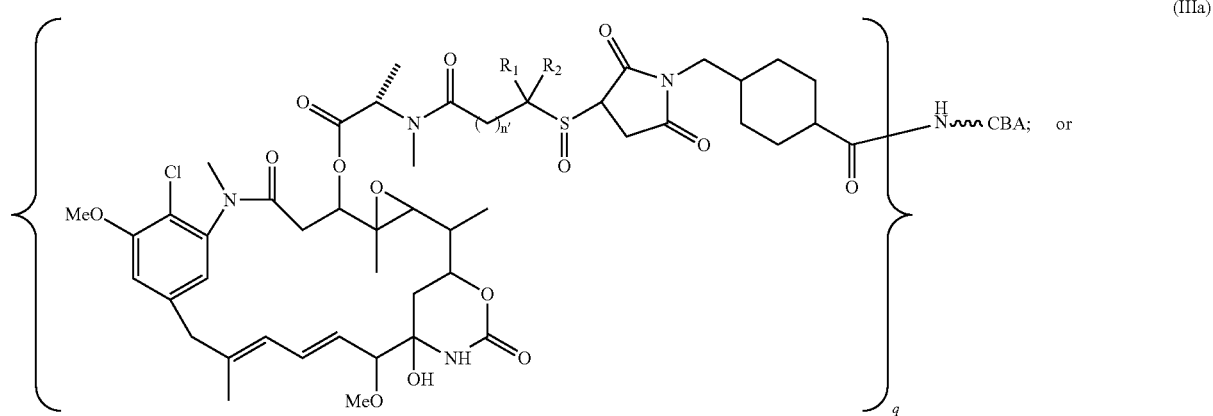

(IIIa)

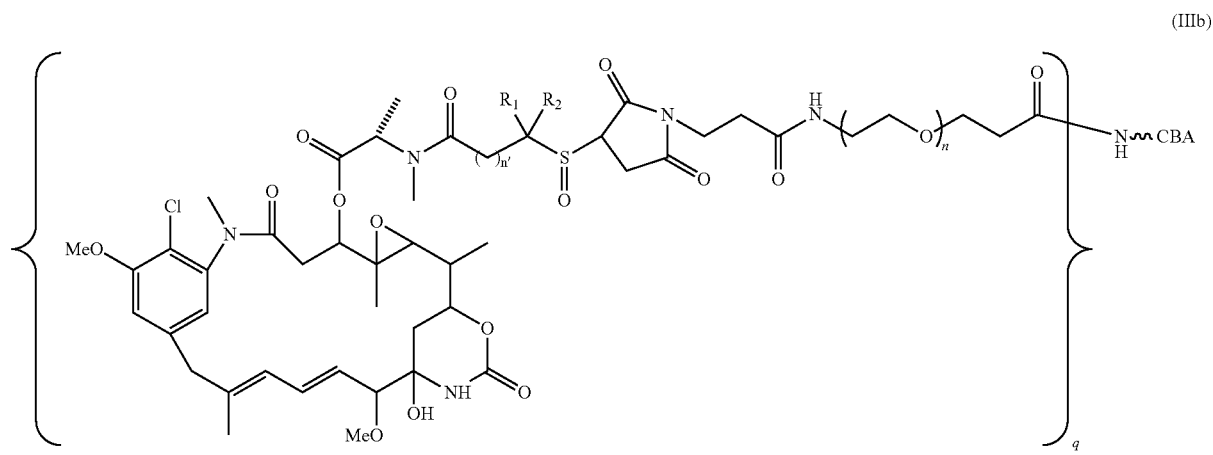

(IIIb)

wherein:
q is an integer from 1 to 20;
n is an integer from 2 to 24;
$R_1$ and $R_2$ are H; and n' is 1; or
$R_1$ and $R_2$ are methyl; and n' is 2.

In another embodiment, the present invention is directed to a cell-binding agent-cytotoxic agent conjugate comprising a cell-binding agent covalently linked to a cytotoxic agent through a sulfoxide linker, wherein the sulfoxide linker is derived from oxidation of a —SH group on the cell-binding agent. In one embodiment, —SH is from a cysteine residue of the cell-binding agent.

In another embodiment, the conjugate is represented by the following structural formula:

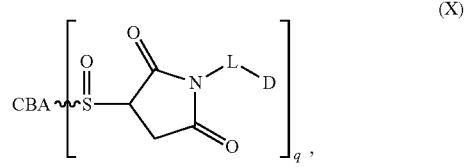

(X)

wherein:
CBA is a cell-binding agent;
D is a cytotoxic agent; and
L is a linker group that covalent links the cytotoxic agent with the cell-binding agent.
More specifically, the sulfoxide group

in structural formula (X) is derived from oxidation of a —SH group of a cysteine residue on the cell-binding agent.

In one embodiment, L is a suitable linker group known in the art. For example, L is a linker group comprising a disulfide group, a thioether group, an acid labile group, a photolabile group, a peptidase labile group, an esterase labile group, or a combination thereof.

In one embodiment, L is derived from a bifunctional crosslinking reagent comprising a maleimide at one end of the bifunctional crosslinking reagent, wherein L represents the remaining portion of the bifunctional crosslinking reagent without the terminal maleimide group. The bifunctional crosslinking reagent is a reagent that possesses two reactive groups, one of which is a maleimide group that reacts with —SH group on the cell-binding agent; while the other one reacts with the cytotoxic agent D. More specifically, the bifunctional crosslinking reagent can be a bifunctional crosslinking reagent described herein. For example, when the bifunctional crosslinking reagent is 1,4-bis-maleimidobutane (BMB) and D is a thiol-containing cytotoxic agent, then L is represented by the following structural formula:

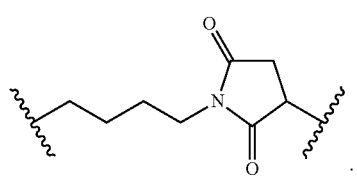 [SMILES: *CCCCN1C(=O)CC(*)C1=O]

In one embodiment, for the conjugate of structural formula (X), D is a maytansinoid. More preferably, D is a maytansinoid represented by structural formula (A1), (A2) or (A3) described above.

In another embodiment, D is auristatin.

Production of the Cytotoxic Compounds and the Cell-Binding Agent-Cytotoxic Compound Conjugates The cytototoxic compounds of the present invention (e.g., compounds of structural formula (I'), (I) and (II)) can be prepared by any suitable methods. In one embodiment, the compounds of structural formula (I') or (I) can be prepared by reacting a compound of structural formula (V') or (V) with an oxidant. Similarly, the compounds of structural formula (II) can be prepared by reacting a compound of structural formula (VI) with an oxidant.

Scheme 1

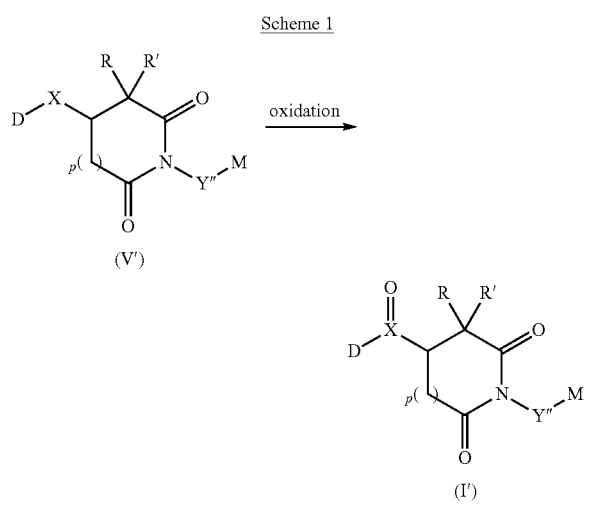

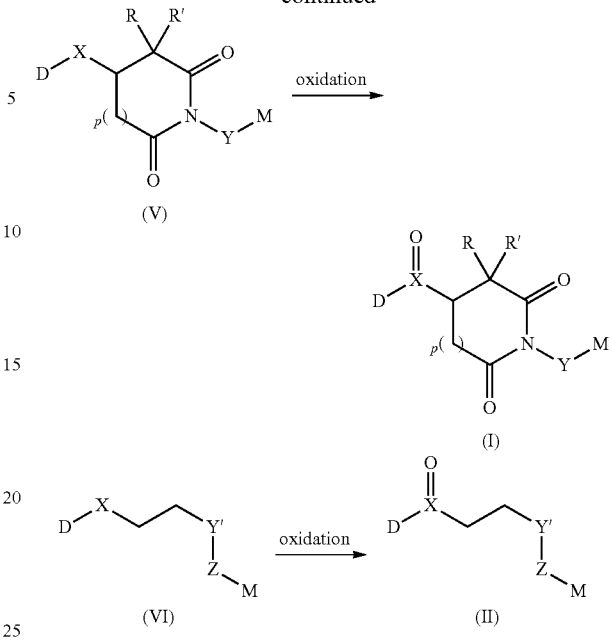

Any suitable oxidant capable of oxidizing a thiol ether group (—S—) to a sulfoxide group (—S(O)—) can be used. Examples of oxidants include, but are not limited to, dimethyldioxirane, $NaIO_4$, t-BuOCl, dioxiranes, calcium hypochlorite $Ca(OCl)_2$, sodium chlorite $NaClO_2$, $HNO_3$ (optionally in the presence of a catalyst, such as a $AuCl_4^-$ catalyst), $O_2$ (in the presence of a catalyst, such as a ceric ammonium nitrate catalyst), acyl nitrites, sodium perborate, organic peroxides (e.g., ROOH, wherein R is a $C_{1-6}$ alkyl), and $H_2O_2$ (optionally in the presence of a catalyst, such as a bis(acetylacetonato)oxovanadium catalyst).

The oxidation reaction can be carried out in a solvent. The solvent can be an organic solvent or mixture of one or more organic solvents, or a mixture of one or more organic solvents with water or an aqueous buffer. Examples of organic solvents can be used include, but are not limited, to dimethylacetimide (DMA), methanol, ethanol, methylene chloride, acetone, DMF, DMSO, ethyl acetate, dioxane, and acetonitrile.

In one embodiment, the oxidation reaction can be carried out in a mixture of dimethylacetimide (DMA) and a succinate buffer. Preferably, the succinate buffer has a pH of about 5. More preferably, the reaction can be carried out in a 60:40 (v:v) mixture of DMA and succinate buffer having a pH about 5.

The oxidation reaction can be carried out at a suitable temperature. In one embodiment, the reaction is carried out at room temperature (about 20-25° C.). Alternatively, the oxidation reaction can be carried out at a low temperature, for example, at about −20° C. to about 15° C. In a preferred embodiment, the oxidation reaction is carried out at about 4° C. In another alternative, the reaction can be carried out at an elevated temperature, for example, higher than about 30° C.

Compounds of formula (V'), (V) and (VI) can be prepared by any suitable methods. In one embodiment, compounds of formula (V'), (V) or (VI) can be prepared by reacting compound D-XH with a bifunctional crosslinking reagent.

In one embodiment, the bifunctional crosslinking reagent comprises a maleimide group (e.g., SMCC, AMAS, BMPS, GMBS, EMCS, SVSB and PEG$_n$-Mal, etc.) and the compound of structural formula (V') or (V) can be prepared according to scheme 2.

Scheme 2

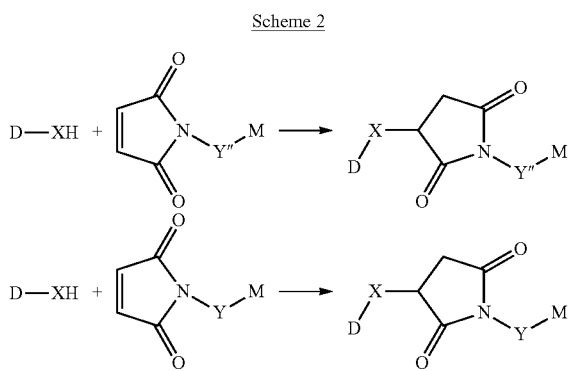

The reaction of D-XH and the bifunctional crosslinking reagent can be carried out in a suitable solvent. The solvent can be an organic solvent or mixture of one or more organic solvents, or a mixture of one or more organic solvents with water or an aqueous buffer. Examples of organic solvents can be used include, but are not limited to, dimethylacetimide (DMA), methanol, ethanol, methylene chloride, acetone, DMF, DMSO, ethyl acetate, dioxane, and acetonitrile.

In one embodiment, the reaction can be carried out in a mixture of dimethylacetimide (DMA) and a succinate buffer. Preferably, the succinate buffer has a pH of about 5. More preferably, the reaction can be carried out in a 60:40 (v:v) mixture of DMA and succinate buffer having a pH about 5.

The reaction can be carried out at a suitable temperature. In one embodiment, the reaction is carried out at room temperature (about 20-25° C.). Alternatively, the oxidation reaction can be carried out at a low temperature, for example, at about −20° C. to about 15° C. In another alternative, the reaction can be carried out at an elevated temperature, for example, higher than about 30° C.

The conjugates of the present invention can be prepared by reacting a cell-binding agent with a compound of the present invention (e.g., compounds of structural formula (I) and (II)) to provide a mixture comprising a cell-binding agent-cytotoxic compound conjugate; the unreacted compound; and reaction side-products. The mixture is optionally purified to provide a purified conjugate.

In another embodiment, the conjugates of the present invention can be prepared through a conjugate oxidation reaction by treating a conjugates of structural formula (VII'), (VII) or (VIII) with an oxidant (see Scheme 3). The values and preferred values for variables depicted in structural formulas (VII'), (VII) and (VIII) are as described above for structural formulas (III'), (III) and (IV), respectively.

Scheme 3

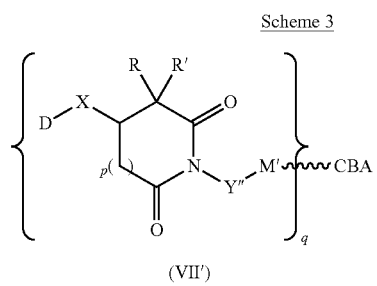

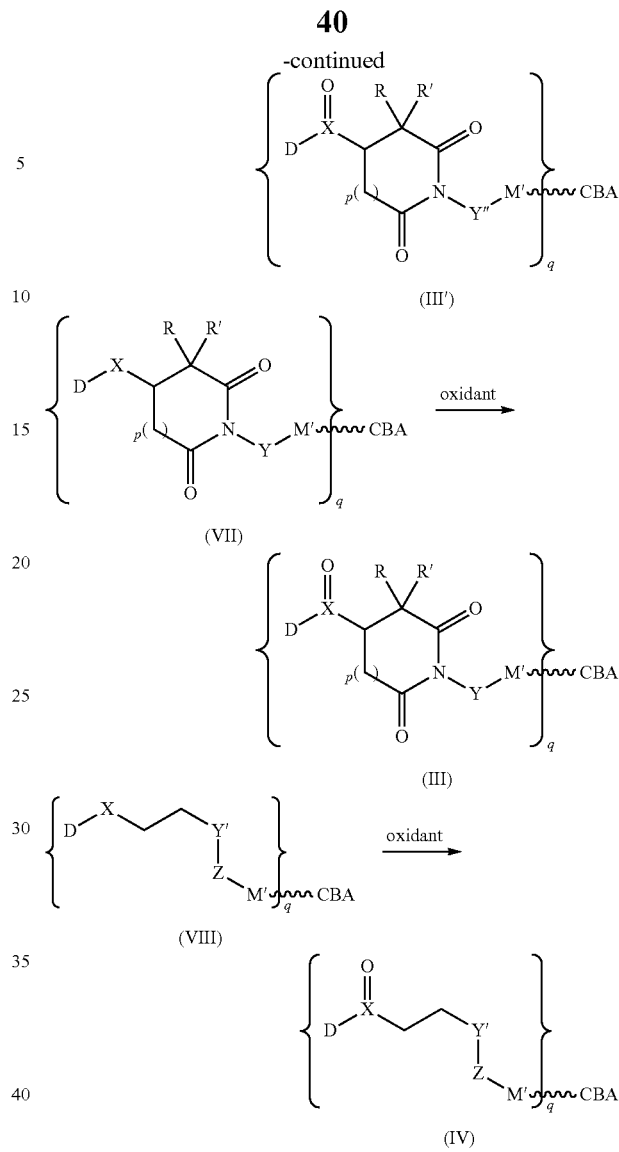

The conjugate of structural formula (X) can be prepared by reacting conjugate comprising a thioether linking group represented by structural formula (XI) with an oxidant.

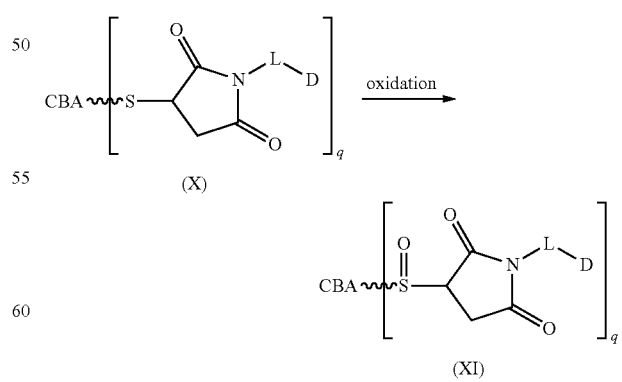

For the conjugate oxidation described above, any suitable oxidant capable of converting a thiol group to a sulfoxide group can be used. Examples of oxidant include, but are not limited to, NaIO$_4$, t-BuOCl, dioxiranes, calcium hypochlorite Ca(OCl)$_2$, sodium chlorite NaClO$_2$, HNO$_3$ (optionally in the presence of a AuCl$_4^-$ catalyst), O$_2$ (in the presence of a ceric ammonium nitrate catalyst), acyl nitrites, sodium perborate, organic peroxides (e.g., ROOH, wherein R is a C$_{1-6}$ alkyl), and H$_2$O$_2$ (optionally in the presence of a bis(acetylacetonato)oxovanadium catalyst). Preferably, the oxidant is H$_2$O$_2$ with a bis(acetylacetonato)oxovanadium catalyst.

The conjugate oxidation reaction can be carried out at a suitable temperature. In one embodiment, the reaction can be carried out at room temperature (about 20-25° C.). Alternatively, the oxidation reaction can be carried out at a low temperature, for example, at about −20° C. to about 15° C. In another alternative, the reaction can be carried out at an elevated temperature, for example, higher than about 30° C. Preferably, the oxidation reaction is carried out at about 4° C. More preferably, the oxidation reaction is carried out at about 4° C. for about 1-12 hours.

In another embodiment, the mixture of the conjugate oxidation reaction is purified immediately after the reaction (e.g., for about 1-12 hours) to remove excess oxidant. Any suitable purification method can be used. In one embodiment, the purification method is as described herein. In another embodiment, the purification method is non-absorptive chromatography and/or dialysis. Preferably, the purification method is non-absorptive chromatography with G25 desalting resin and/or dialysis at 4° C.

Any suitable purification methods can be used for purifying the mixture comprising the conjugates of the present invention. In one embodiment, the mixture can be purified using tangential flow filtration (TFF), e.g., a membrane-based tangential flow filtration process, non-adsorptive chromatography, adsorptive chromatography, adsorptive filtration, or selective precipitation, or any other suitable purification process, as well as combinations thereof. One of ordinary skill in the art will appreciate that purification after the conjugation step enables the isolation of a stable conjugate comprising the cell-binding agent chemically coupled to the cytotoxic agent.

Any suitable TFF systems may be utilized for purification, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (J T Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., Mab-Select, GE Healthcare, Piscataway, N.J.), where the cell-binding agent is an antibody, and lectin affinity resins, e.g. Lentil Lectin Sepharose resin (GE Healthcare, Piscataway, N.J.), where the cell-binding agent bears appropriate lectin binding sites. Alternatively an antibody specific to the cell-binding agent may be used. Such an antibody can be immobilized to, for instance, Sepharose 4 Fast Flow resin (GE Healthcare, Piscataway, N.J.). Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

In Vitro Cytotoxicity

The cytotoxic compounds and cell-binding agent-cytotoxic agent conjugates of the invention can be evaluated for their ability to suppress proliferation of various cancer cell lines in vitro. For example, cell lines such as the squamous cell carcinomal line A431, the lung carcinoma line PC9, the human colon carcinoma line COLO 205, the rhabdomyosarcoma cell line RH-30, and the multiple myeloma cell line MOLP-8 can be used for the assessment of cytotoxicity of these compounds and conjugates. Cells to be evaluated can be exposed to the compounds or conjugates for 1-5 days and the surviving fractions of cells measured in direct assays by known methods. IC$_{50}$ values can then be calculated from the results of the assays. Examples of in vitro potency and target specificity of antibody-cytotoxic agent conjugates of the present invention are shown in FIGS. 1 and 2.

Compositions and Methods of Use

The present invention includes a composition (e.g., a pharmaceutical composition) comprising novel cytotoxic compounds described herein (e.g., compounds of structural formula (I'), (I) and (II)), derivatives thereof, or conjugates thereof, (and/or solvates, hydrates and/or salts thereof) and a carrier (a pharmaceutically acceptable carrier). The present invention also includes a composition (e.g., a pharmaceutical composition) comprising novel cytotoxic compounds described herein (e.g., compounds of structural formula (I'), (I) and (II)), derivatives thereof, or conjugates thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human). The present compositions are also useful for treating depression, anxiety, stress, phobias, panic, dysphoria, psychiatric disorders, pain, and inflammatory diseases in a mammal (e.g., human).

In one embodiment, the present invention includes a composition or a pharmaceutical composition comprising the conjugates described herein (e.g., conjugates of structural formula (III'), (III) or (IV), wherein the average molar ratio of the cytotoxic agent to the cell-binding agent of the conjugates in the composition is about 1 to about 10, about 2 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, about 4.5 to 5.5 (e.g., about 4.5, about 4.6, about 4.7, about 4.8, about 4.9, about 5.0, about 5.1, about 5.2, about 5.3, about 5.4, about 5.5).

The present invention also includes a method of inhibiting abnormal cell growth or treating a proliferative disorder in a mammal (e.g., human) comprising administering to said mammal a therapeutically effective amount of cytotoxic compounds described herein (e.g., compounds of structural formula (I'), (I) and (II)), derivatives thereof, or conjugates thereof (e.g., conjugates of structural formula (III'), (III) or (IV)), (and/or solvates and salts thereof) or a composition thereof, alone or in combination with a second therapeutic agent.

The present invention also provides methods of treatment comprising administering to a subject in need of treatment a therapeutically effective amount of any of the conjugates described above.

Similarly, the present invention provides a method for inducing cell death in selected cell populations comprising contacting target cells or tissue containing target cells with an effective amount of a cell-binding agent-cytotoxic compound conjugate of the present invention, a salt (e.g., pharmaceutically acceptable salt) or solvate thereof. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 µM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic conjugate of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 ml of normal saline to which 5 to 10 ml of human serum albumin can be added. Dosages will be 10 µg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer of the lung (small cell and non-small cell), breast, colon, brain, prostate, kidney, pancreas, ovary, head and neck, skin (melanoma), Merkel cell carcinoma, glioblastoma, neuroblastoma, and cancers of lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include:

Comprehensive index
By Manufacturer
Products (by company's or trademarked drug name)
Category index
Generic/chemical index (non-trademark common drug names)
Color images of medications Product information, consistent with FDA labeling
Chemical information
Function/action
Indications & Contraindications
Trial research, side effects, warnings
Analogues and Derivatives One skilled in the art of cytotoxic compounds will readily understand that each of the cytotoxic compound described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

EXEMPLIFICATION

Example 1

General Methods for Preparing Conjugates of the Present Invention

Method 1:

A thiol-containing cytotoxic agent (e.g., D-SH) is reacted with a maleimide containing heterobifunctional linker (e.g., AMAS, BMPS, GMBS, EMCS, SBSV, PEG$_n$-Mal) in a mixture of dimethylacetimide (DMA) and 50 mM succinate buffer pH 5 (60:40 DMA:buffer by volume) for 5 min to generate a succinimidyl thioether. The mixture is then treated with mild oxidant (e.g., hydrogen peroxide, dimethyldioxirane) at 4° C., which selectively converts thioether into sulfoxide and not the sulfone. The mixture is then added to an antibody solution buffered at pH about 6-9 in a 3-7 fold molar excess (based on linker concentration) and the reaction was allowed to proceed overnight to generate the sulfoxide linker conjugate.

Method 2:

An antibody-cytotoxic agent conjugate comprising a thioether group (preferably a succinimidyl thioether group) is treated at pH 7.4 with 3-100 mole % of an oxidant (e.g., NaIO$_4$, t-BuOCl, dioxiranes, calcium hypochlorite Ca(OCl)$_2$, sodium chlorite NaClO$_2$, HNO3 and a AuCl$_4^-$ catalyst, O$_2$ and ceric ammonium nitrate catalyst, acyl nitrites, sodium perborate, and organic peroxides ROOH and H$_2$O$_2$ with a bis(acetylacetonato)oxovanadium catalyst). Conjugate oxidation is done at 4° C. for 1-12 hours followed by immediate removal of excess oxidant using G25 desalting resin and/or dialysis.

Conjugates made by method 1 or 2 can be assayed for extent of thioether oxidation to sulfoxide by kinetic trapping of the released sulfenic acid intermediate. An exemplary procedure for kinetic trapping is described below in Example 2.

The invention will now be illustrated by reference to non-limiting examples. Unless otherwise stated, all percents, ratios, parts, etc. are by weight. Hydrogen peroxide (30% w/v in water), N-ethyl maleimide, and 5,5-dimethyl-1,3,-cyclohexanedione (dimedone) were purchased from Sigma. Antibody drug conjugates (Ab-SMCC-DM1, Ab-PEG$_4$-mal-DM1, Ab-PEG$_4$-mal-DM4) were prepared according to published methods (Kovtun, et al, *Cancer Research*, 2010, 70, 2528-37). A Bruker ESQUIRE™ 3000 ion trap mass spectrometer was used to obtain mass spectra for all reaction products and was used in line with a Water 2695 series HPLC. Samples were analyzed using the analytical reverse phase HPLC method described below:

Column: Vydac C8 (208TP104), 250×4.6 mm, 5 micron. Temperature: 25° C.
Flow rate: 1.0 mL/min Injection volume: 50 microliters
Absorbance detection: 252 nm
Linear gradient of 80% A 80% B over 30 min
Solvent A: water (0.025% formic acid)
Solvent B: acetonitrile (0.025% formic acid)

Mass Spectrometer Conditions
Ionization method: Electrospray; Nebulizer gas flow: 25 psi;
Drying temperature: 350° C.; Heating gas flow: 8.0 L/min;
Mass range: 50-2000
MS detection in alternating positive and negative ion modes or in MS$^2$ mode.

Example 2

Selective Oxidation of Ab-SMCC-DM1 to Sulfoxide Linked Conjugate 2 chB38.1-SMCC-DM1 (9 µM in PBS, pH 7.4) was treated with 1 µM hydrogen peroxide and 5 mole % bis(acetylacetonato)oxovanadium catalyst at 4° C. for 4 h. To remove excess oxidant, gel fitration of the conjugate into a G25 Sephadex (GE healthcare) column equilibrated in 10 mM sodium citrate pH 5.5 followed by dialysis (2 exchanges in a slide-a-lyzer cassette) was carried out. The oxidized conjugate was assayed for maytansine per antibody ratio (MAR), % monomer, and % unconjugated free maytansinoid and the sample was identical to the parent conjugate (3.7 MAR, 0.1% free maytansinoid, 95% monomer).

In Vitro Cytotoxicity Assays Comparing Activity of Conjugate 1 (Ab-SMCC-DM1) and Selectively Oxidized Conjugate 2

Confluent T75 flasks of PC9 cells (for anti-EPCAM-SMCC-DM1) and A431 cells (for anti-EGFR-SMCC-DM1) grown in growth medium (DMEM (Invitrogen) containing 10% fetal bovine serum (ATCC), 2 mM L-glutamine (Invitrogen), and penicillin-streptomycin (Invitrogen) were detached with 0.25% tryspin-EDTA (Invitrogen), stained with trypan blue (Invitrogen) and the number of live cells was counted on a hemacytometer. Between 1000 and 2000 cells/well were seeded in 96-well flat-bottom tissue culture plates (Falcon) in growth media and allowed to adhere overnight at 37° C. All cells were obtained from ATCC. After 1 day, cells were continuously exposed to anti-EpCAM or anti-EGFR antibody conjugates (1 and 2) for 96 hr at 37° C. at concentrations of 2 pM to 30 nM (3-fold serial dilutions). Blocking controls were performed in parallel where cells were treated for 1 hr at 37° C. with 1 µM unconjugated antibody in fresh growth media prior to conjugate exposure. Each test condition was performed in triplicate. After conjugate treatment, 20 µl WST-8 reagent (Dojindo Molecular) was added to each well and incubated at 37° C. for 1-5 h for color development. The plate absorbance was measured at 450 nm and used to calculate the surviving cell fraction (compared with untreated control cells). The IC$_{50}$ values were estimated from plots of conjugate concentration (M) versus surviving cell fraction. Cytotoxicity data shown in FIGS. 1 and 2. FIG. 1 shows that anti-EGFR antibody conjugate IgG1-sulfoxide-DM1 conjugate 2 is ~2-fold more potent than the parent IgG1-SMCC-DM1 conjugate 1. FIG. 2 shows that anti-EpCAM-SMCC-sulfoxide-DM1 conjugate 2 is ~3-fold more potent than the parent anti-EpCAM-SMCC-DM1 conjugate 1. Preincubation of PC9 cells with 1 μM unconjugated anti-EpCAM antibody (to fully block antigen binding sites) leads to significant reduction in cell killing activity for conjugates 1 and 2. Therefore, the data suggest that the additional activity observed for conjugate 2 is antigen-dependent.

Characterization of Oxidized Thioether in Conjugate 2

Conjugates made by method 1 or 2 were assayed for extent of thioether oxidation to sulfoxide by kinetic trapping of the released sulfenic acid intermediate. Sulfoxide linker conjugate 2 (36 μM) was incubated with 10 mM dimedone (12 h, 37° C., PBS, pH 7.4). Free maytansinoid species were then acetone extracted and identified by LC-MS and quantified (by integrated area at 252 nm and comparison to a standard curve). Presence of maytansinoid-dimedone adduct (i.e. DM1-dimedone) was evidence of oxidation of the thioether ether linkage selectively to the sulfoxide. Data shown in FIG. 4.

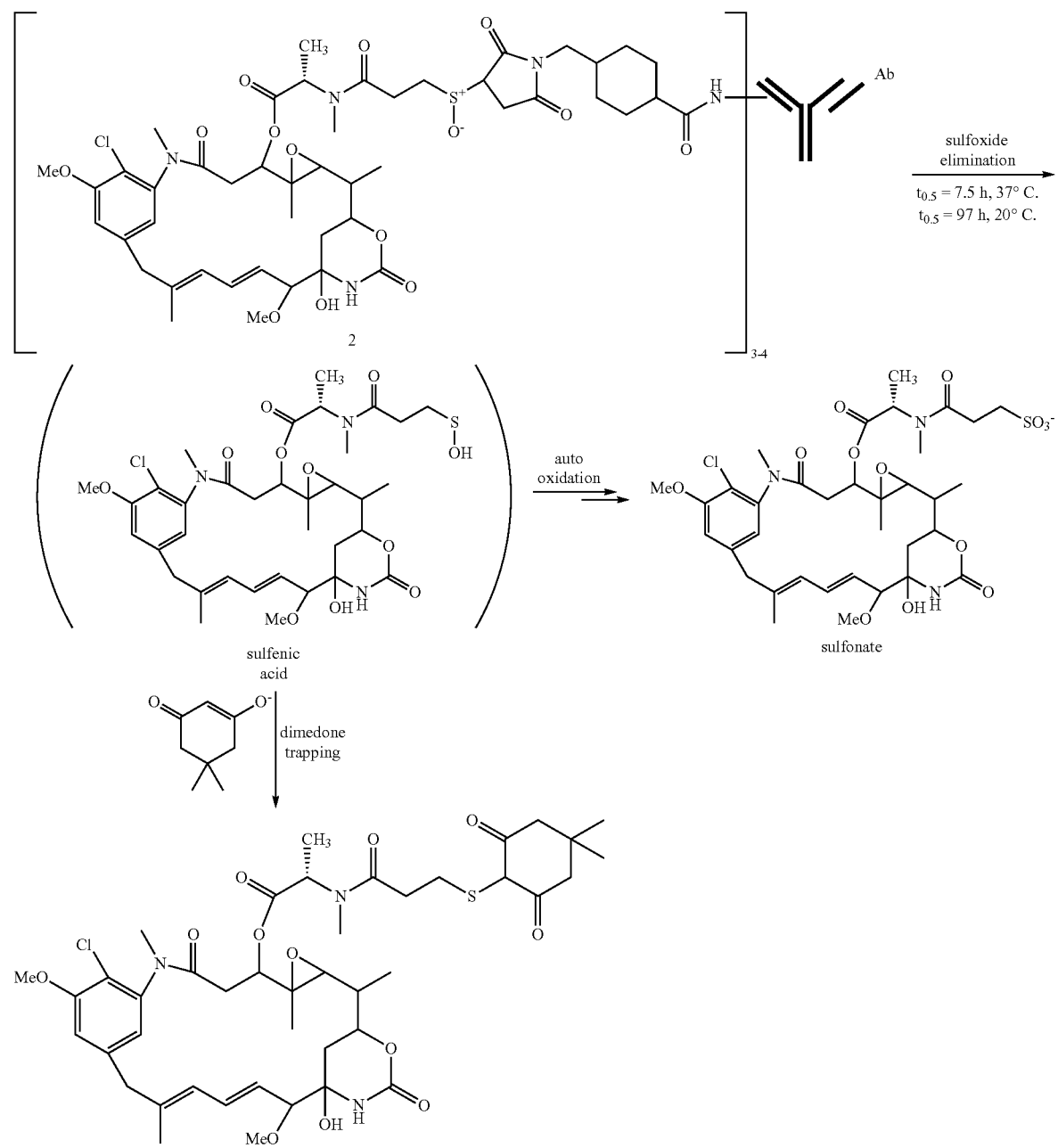

Example 3

Oxidation Promoted Release of Maytansinoids from Thioether Linker Ab-PEG$_4$-mal-DM$_x$ Ab-PEG$_4$-mal-DM1 and Ab-PEG$_4$-mal-DM4 (36 μM, average of 4 maytansinoids per antibody) with no detectable unconjugated maytansinoid was treated with hydrogen peroxide (0.1 μM-50 μM final concentration) at pH 7.4 (PBS)

for 12 h at 37° C. Increase in free maytansinoids was quantified using a mixed-mode chromatography method (Fleming, et al, *Analytical Biochemistry*, 2005, 340, 272). Briefly, a HISEP shielded hydrophobic phase column (5 μm particle size, 4.6×250 mm length, Supelco, Bellefonte, Pa., USA) was used for analyzing Ab-DM1 conjugates. Detection was at 252 and 280 nm (extracted from PDA spectra). The flow rate was 0.7 ml/min. Mobile phase A consisted of 100 mM ammonium acetate (pH 7.0). Mobile phase B was 100% acetonitrile. The column was equilibrated at 25% B followed by a linear gradient over 25 min to 40% B after sample injection. Intact conjugate elutes between 2-5 min while released maytansinoid is detected between 10-25 min. Data shown in FIG. 5C.

Example 4

Rate of Oxidation of DM1-NEM and DM4-NEM

10 μM DM1-NEM or DM4-NEM (95% PBS pH 7.4, 5% dimethylacetamide) were treated at room temperature with 1 mM hydrogen peroxide and reaction aliquots (30 μl) were injected directly onto RP-HPLC at various time points from 0-400 min. Maytansinoid products were quantified by measuring integrated area under the curve at 252 nm and comparison to a calibration curve with known standards. Kinetic data shown in FIG. 5A.

Example 5

Rate of Sulfoxide Elimination of DM1-SO-NEM and DM4-SO-NEM

8 μM DM1-SO-NEM or DM4-SO-NEM (95% PBS pH 7.4, 5% dimethylacetamide) were incubated at 37° C. and reaction aliquots (50 μl) were injected directly onto RP-HPLC at various time points from 0-12 h. Maytansinoid products were quantified by measuring integrated area under the curve at 252 nm and comparison to a calibration curve with known standards. Kinetic data shown in FIG. 5B.

Thioether formed with hindered thiol DM4 oxidizes 2-fold slower (FIG. 5A) and undergoes sulfoxide elimination 2-fold slower than corresponding thioether formed from unhindered DM1 thiol (FIG. 5B). The observation that Ab-PEG4-mal-DM4 is ~5-fold more resistant to oxidation promoted free maytansinoid release than Ab-PEG4-mal-DM1 (FIG. 5C) is consistent with the observed rates of sulfoxide formation and beta-elimination.

I claim:

1. A compound represented by the following structural formula:

wherein:
D is a cytotoxic agent;
X is S or Se;
R and R' are each independently selected from the group consisting of —H, an alkyl, a cycloalkyl, —OR$^a$, and —NR$^b$R$^c$;
R$^a$, R$^b$ and R$^c$ are each independently H or an alkyl;
p is 0, 1 or 2
Y is an alkylene, a polyethylene glycol unit represented by —(CH$_2$—CH$_2$—O)$_n$—R$^d$—, —R$^d$-E- or —R$^d$—W—R$^e$—,
n is an integer from 1 to 24;
E is a cycloalkyl, a heterocyclyl, an aryl or a heteroaryl,
W is —C(=O)NH—, —NHC(=O)—, —(C=O)O— or —O(C=O)—,
R$^d$ is absent or an alkyl;
R$^e$ is an alkyl;
M is a linking group that can react with a cell-binding agent to form a covalent bond.

2. The compound of claim 1, wherein D is a maytansinoid.

3. The compound of claim 2, wherein D is represented by the following structural formula:

wherein:
Y$_1$ represents (CR$_7$R$_8$)$_l$(CR$_5$R$_6$)$_m$(CR$_3$R$_4$)$_n$CR$_1$R$_2$—,
R$_1$, R$_2$, R$_3$, R$_4$, R$_5$, R$_6$, R$_7$ and R$_8$ are each independently H, an alkyl, an alkenyl, a cycloalkyl, a heteroaryl, a heterocyclyl, or an aryl; and
l, m and n are each independently 0 or an integer from 1 to 5.

4. The compound of claim 3, wherein R$_1$ and R$_2$ are each independently H, C$_{1-4}$ alkyl or C$_{1-4}$ alkyl substituted with one to six halogens.

5. The compound of claim 4, wherein R$_1$ and R$_2$ are each independently H, methyl, —CF$_3$ or —CCl$_3$.

6. The compound of claim 4, wherein R$_1$ and R$_2$ are both H or methyl.

7. The compound of claim 3, wherein l and m are 0, n is 1, R$_1$, R$_2$, R$_3$ and R$_4$ are all H.

8. The compound of claim 3, wherein n is 0, l and m are both 1, R$_5$, R$_6$, R$_7$ and R$_8$ are all H, R$_1$ and R$_2$ are both methyl.

9. The compound of claim 3, wherein n is 0, l and m are both 1, R$_1$, R$_5$, R$_6$, R$_7$ and R$_8$ are all H, and R$_2$ is methyl.

10. The compound of claim 1, wherein X is S.

11. The compound of claim 1, wherein p is 0.

12. The compound of claim 1, wherein one of R and R' is H, and the other is H, a C$_{1-4}$ alkyl, —OR$^a$, or —NR$^b$R$^c$, wherein R$^a$, R$^b$ and R$^c$ are each independently H or a C$_{1-4}$ alkyl.

13. The compound of claim 12, wherein R and R' are both H.

14. The compound of claim 1, wherein Y is a C$_{1-6}$ alkylene, a polyethylene glycol unit represented by —(CH$_2$—CH$_2$—O)$_n$—R$^d$—, —R$^d$-E- or —R$^d$—W—R$^e$—, wherein R$^d$ is absent or a C$_{1-4}$ alkyl; R$^e$ is a C$_{1-4}$ alkyl; W is —C(=O)NH—; E is cyclohexyl and n is an integer from 2 to 8.

15. The compound of claim 14, wherein Y is

16. The compound of claim 1, wherein M represents a maleimide, a haloacetamido, —SH, —SSR$^f$, —CH$_2$SH, —CH(Me)SH, —C(Me)$_2$SH, —NHR$^g$, —CH$_2$NHR$^g$, —NR$^g$NH$_2$, —COOH, a reactive ester, an amino acid or a peptide comprising 2 to 10 amino acids, wherein R$^f$ is selected from phenyl, nitrophenyl, dinitrophenyl, carboxynitrophenyl, pyridyl or nitropyridyl and R$^g$ is —H or a C$_{1-4}$ alkyl.

17. The compound of claim 16, M represents a maleimide, haloacetamido, N-hydroxysuccinimde ester, N-hydroxy sulfosuccinimide ester, nitrophenyl ester, dinitrophenyl ester, sulfo-tetraflurophenyl ester or pentafluorophenyl ester.

18. The compound of claim 17, wherein M represents a N-hydroxysuccinimide ester.

* * * * *